(12) United States Patent
Sutton

(10) Patent No.: US 12,181,461 B2
(45) Date of Patent: Dec. 31, 2024

(54) BLOOD SEPARATION AND ANALYSIS DEVICE AND METHODS

(71) Applicant: 1866402 ONTARIO LIMITED, Sudbury (CA)

(72) Inventor: Jeffrey Sutton, Sudbury (CA)

(73) Assignee: 1866402 Ontario Limited, Sudbury (CA)

( * ) Notice: Subject to any disclaimer, the term of this patent is extended or adjusted under 35 U.S.C. 154(b) by 745 days.

(21) Appl. No.: 17/421,333

(22) PCT Filed: Jan. 7, 2020

(86) PCT No.: PCT/CA2020/050013
§ 371 (c)(1),
(2) Date: Jul. 7, 2021

(87) PCT Pub. No.: WO2020/142839
PCT Pub. Date: Jul. 16, 2020

(65) Prior Publication Data
US 2022/0065845 A1 Mar. 3, 2022

Related U.S. Application Data

(60) Provisional application No. 62/789,357, filed on Jan. 7, 2019.

(51) Int. Cl.
*B01L 3/00* (2006.01)
*C12Q 1/44* (2006.01)
(Continued)

(52) U.S. Cl.
CPC .......... *G01N 33/5002* (2013.01); *B01L 3/502* (2013.01); *B01L 3/502715* (2013.01);
(Continued)

(58) Field of Classification Search
CPC ..... B01L 2200/0652; B01L 2200/0684; B01L 2200/0689; B01L 2200/16;
(Continued)

(56) References Cited

U.S. PATENT DOCUMENTS 3,254,527 A 6/1966 Noller
3,661,265 A 5/1972 Greenspan
(Continued)

FOREIGN PATENT DOCUMENTS

CN 200480041700.X 2/2007
EP 3206009 A1 6/2017
(Continued)

OTHER PUBLICATIONS

European Patent Office, Supplemental European Search Report, EP 20738902, dated Jun. 21, 2022, DE.
(Continued)

*Primary Examiner* — Jill A Warden
*Assistant Examiner* — Michael Stanley Gzybowski
(74) *Attorney, Agent, or Firm* — Reichel Stohry Dean LLP; Natalie J. Dean

(57) ABSTRACT

There is provided a device and method for separation of blood, including sedimentation of plasma using PVA. The device comprises an inner container enclosed in an outer container, wherein upon alignment of respective openings, allows sample to exit from the inner container into a reaction structure. The reaction structure comprises one or more layers, each with one or more portions each containing concentrations of one or more chemicals.

12 Claims, 20 Drawing Sheets

(51) Int. Cl.

| | |
|---|---|
| *C12Q 1/50* | (2006.01) |
| *G01N 1/38* | (2006.01) |
| *G01N 1/40* | (2006.01) |
| *G01N 15/06* | (2006.01) |
| *G01N 33/50* | (2006.01) |
| *G01N 33/70* | (2006.01) |
| *G01N 15/01* | (2024.01) |
| *G01N 15/075* | (2024.01) |

(52) U.S. Cl.
CPC ............... *B01L 3/527* (2013.01); *C12Q 1/44* (2013.01); *C12Q 1/50* (2013.01); *G01N 1/38* (2013.01); *G01N 1/4077* (2013.01); *G01N 15/06* (2013.01); *G01N 33/70* (2013.01); *B01L 2200/025* (2013.01); *B01L 2200/026* (2013.01); *B01L 2200/0631* (2013.01); *B01L 2200/0652* (2013.01); *B01L 2200/0684* (2013.01); *B01L 2200/0689* (2013.01); *B01L 2200/16* (2013.01); *B01L 2300/042* (2013.01); *B01L 2300/047* (2013.01); *B01L 2300/0609* (2013.01); *B01L 2300/0832* (2013.01); *G01N 2001/386* (2013.01); *G01N 2001/4083* (2013.01); *G01N 15/01* (2024.01); *G01N 15/075* (2024.01)

(58) Field of Classification Search
CPC ......... B01L 2300/042; B01L 2300/047; B01L 2300/0609; B01L 2300/0832; G01N 2001/386; G01N 2001/4083
See application file for complete search history.

(56) References Cited

U.S. PATENT DOCUMENTS

| | | | |
|---|---|---|---|
| 4,473,530 A * | 9/1984 | Villa-Real | B01L 3/50825 73/863.52 |
| 5,738,784 A | 4/1998 | Holm et al. | |
| 6,099,730 A | 8/2000 | Ameer et al. | |
| 7,271,007 B2 | 9/2007 | Weigl et al. | |
| 7,282,179 B2 | 10/2007 | Iwaki et al. | |
| 7,531,362 B2 | 5/2009 | Chan | |
| 7,572,640 B2 | 8/2009 | Goix et al. | |
| 8,018,593 B2 | 9/2011 | Tan et al. | |
| 8,263,024 B2 | 9/2012 | Wan et al. | |
| 8,821,814 B2 | 9/2014 | Cho et al. | |
| 8,883,518 B2 | 11/2014 | Roy et al. | |
| 9,108,195 B2 | 8/2015 | Herr et al. | |
| 9,176,105 B2 | 11/2015 | Mace et al. | |
| 9,341,620 B2 | 5/2016 | Lowe et al. | |
| 9,643,180 B2 | 5/2017 | Abrams et al. | |
| 2003/0205538 A1 | 11/2003 | Dorian et al. | |
| 2009/0181412 A1 | 7/2009 | Cho et al. | |
| 2011/0212002 A1 * | 9/2011 | Curry | B01L 3/50825 422/430 |
| 2012/0220047 A1 | 8/2012 | Seifried et al. | |
| 2014/0234949 A1 | 8/2014 | Wasson et al. | |
| 2014/0342371 A1 | 11/2014 | Holmes | |
| 2016/0174888 A1 | 6/2016 | Berthier et al. | |
| 2016/0270636 A1 | 9/2016 | Egeland | |
| 2016/0310904 A1 | 10/2016 | Liu et al. | |
| 2016/0361715 A1 | 12/2016 | Shi et al. | |
| 2017/0122846 A1 | 5/2017 | Holmes et al. | |
| 2017/0248508 A1 | 8/2017 | Ward et al. | |
| 2017/0336307 A1 | 11/2017 | Distel et al. | |
| 2017/0354361 A1 | 12/2017 | Tan et al. | |
| 2018/0133714 A1 | 5/2018 | Wo et al. | |
| 2019/0111423 A1 * | 4/2019 | Ismagilov | B01L 3/502753 |

FOREIGN PATENT DOCUMENTS

| | | |
|---|---|---|
| WO | 2016105508 A2 | 6/2016 |
| WO | 2017040966 A1 | 3/2017 |

OTHER PUBLICATIONS

Levine and Hoyt, The Use of Pectin and Gelatin in the Processing of Plasma in the Blood Bank, American Journal of Clinical Pathology 16(1): 40-44 and abstract, Jan. 1, 1946, US.

Intellectual Property Office India, Examination Report, Indian Application No. 202117035271, dated Feb. 21, 2023, IN.

Levine, M.G., and Hoyt, R.E., The Use of Pectin and Gelatin in the Processing of Plasma in the Blood Bank, American Journal of Clinical Pathology, vol. 16, Issue 1, Jan. 1, 1946, pp. 40-44, Abstract, US.

Canadian Intellectual Property Office, International Search Report for PCT/CA2020/050013, Mar. 23, 2020, CA.

Canadian Intellectual Property Office, Written Opinion of the International Searching Authority for PCT/CA2020/050013, Mar. 23, 2020, CA.

* cited by examiner

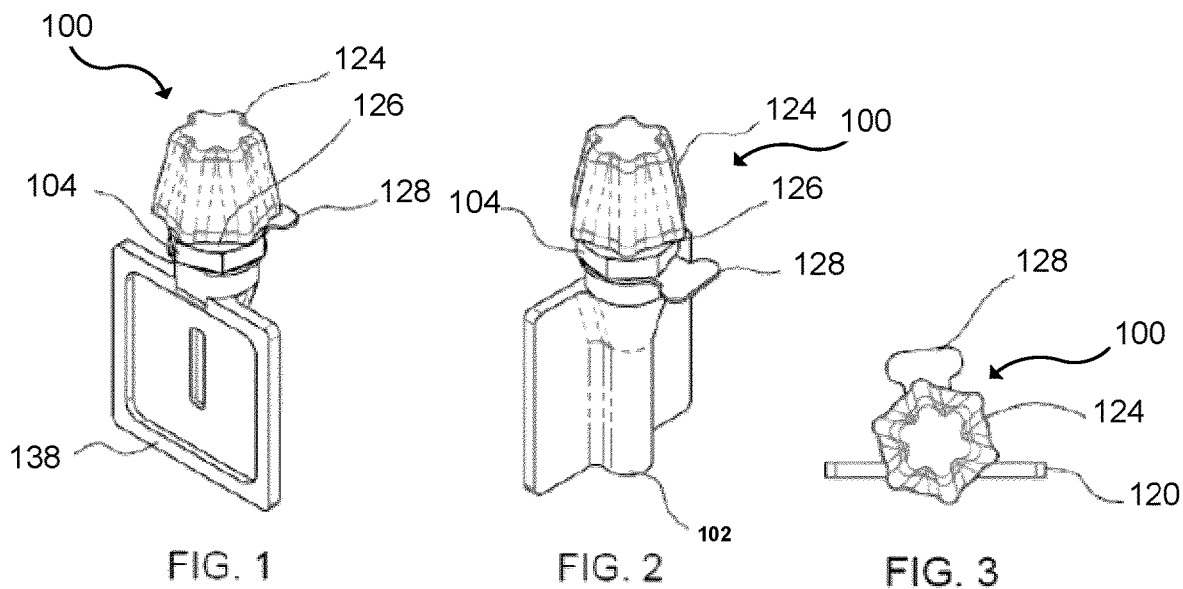
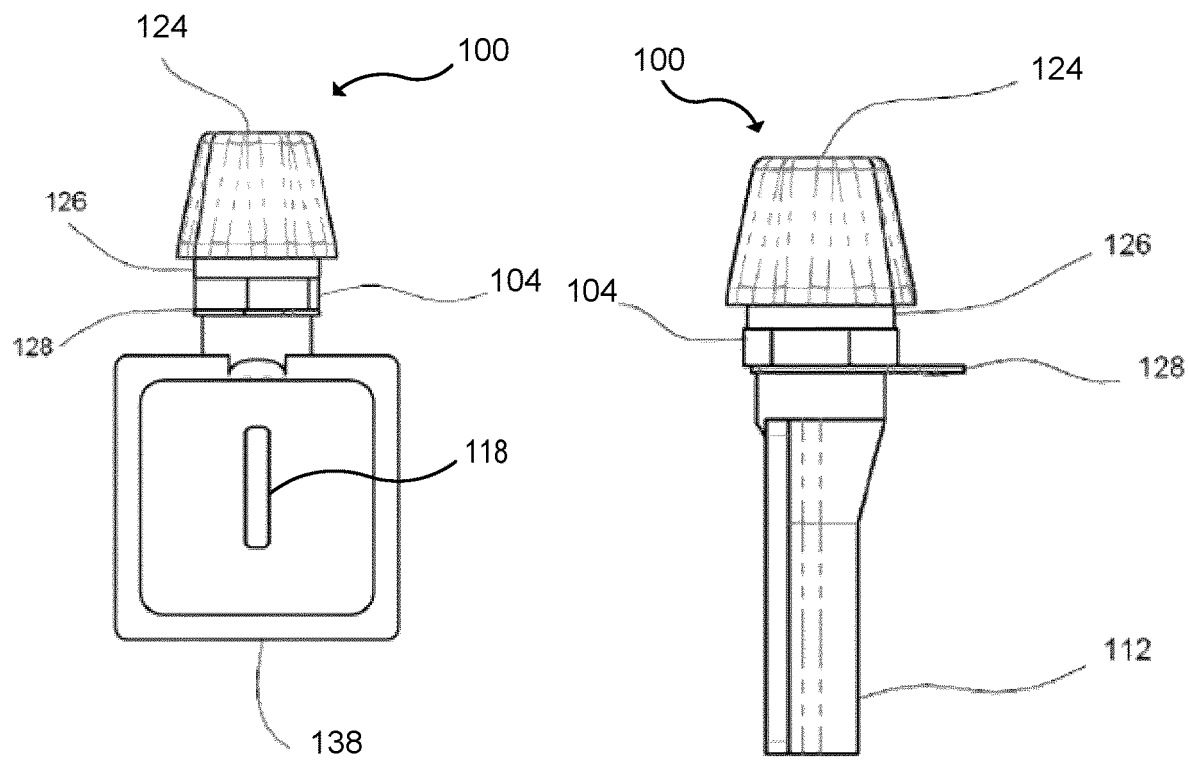

SECTION A-A

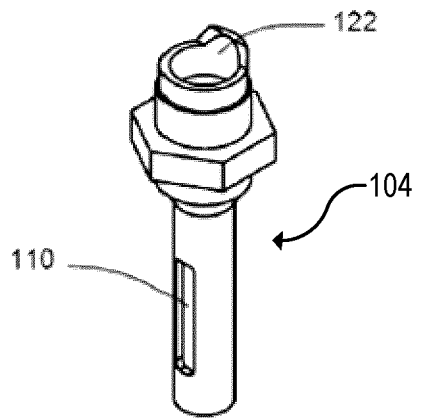
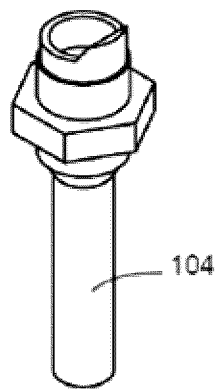
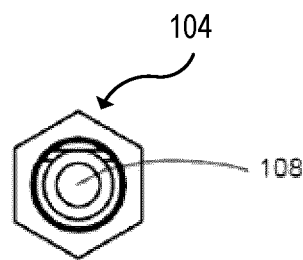
FIG. 20　　　　FIG. 21　　　　FIG. 22
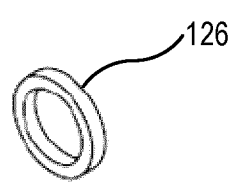
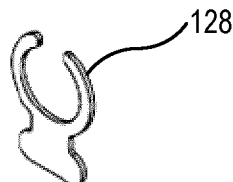
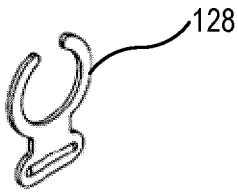
FIG. 23　　　　FIG. 24A　　　　FIG. 24B

BLOOD SEPARATION AND ANALYSIS DEVICE AND METHODS

PRIORITY

The present application is related to, claims the benefit of priority to, and is a 35 U.S.C. 371 national stage application of International Patent Application Serial No. PCT/CA2020/050013, filed Jan. 7, 2020, which claims the priority benefit of U.S. Provisional Patent Application No. 62/789,357 filed on Jan. 7, 2019. The entire contents of each of the aforementioned priority applications are hereby expressly incorporated by reference herein in their entireties.

TECHNICAL FIELD

The improvements generally relate to the field of blood separation and analyte analysis.

BACKGROUND

Biochemistry Testing

For health monitoring, disease diagnosis, and illness management for humans, and animals, biochemistry testing is common. Much of this testing requires the collection of whole blood, separation of the liquid plasma from the cellular matter, aliquoting/dilution, distribution, and then using various biochemistry methods and analytics to measure one or more analytes such as Creatinine, Albumin, Vitamin D etc. in the plasma. In a typical scenario, 3 ml or more of venous blood is collected into vacutainer tubes by a technically trained and certified specialist (phlebotomist or nurse), spun in a centrifuge at 1500 times gravity for about 12 minutes to speed up the natural tendency of blood to sediment, causing the more dense cellular components of blood (erythrocytes: 37-52% typical by volume, leukocytes: 1%, and thrombocytes: <1%) to settle to the bottom, after which the plasma (the remaining liquid) can be carefully collected off the top. Then, again by a technician, the plasma is aliquoted, diluted as needed, and distributed into instrument-specific vials for analysis by a myriad of biochemistry analytic devices (analysers). Typically this testing process takes place in a controlled laboratory environment and can take anywhere from 1 hour to a number of hours depending on the approach. With all analysers periodic calibration is required to ensure ongoing accuracy of the instrument.

Microfluidic Testing

More recently, to better allow testing near to the person to be tested, lessen the impact on the testee, and speed up reporting, tests using capillary blood (a few drops of blood, approximately 50-200 microliters (ul), taken from a finger prick) have become popular. Concurrent with this is the concept of a single use, disposable 'lab on a chip'. There are a number of challenges with this concept, but primarily it is that it is difficult to quickly collect more than a 100 ul of whole blood and the amount actually obtained is so little that it is hard to separate and properly distribute for testing. It is also difficult to manage fluid flow for such small volumes.

A number of companies may sell devices that function by placing the whole blood into mini-centrifuges, duplicating the central lab process, or placing the whole blood in disk that is designed to be spun, also separating the plasma by centrifugal forces. In this technology the plasma can be distributed as required through valving and channeling making the disks somewhat complicated and expensive. Multiple tests, or panels, can be performed on this equipment but these devices typically still require technical expertise to operate, are mechanical in nature, therefore more costly and with a higher failure rate than any passive device.

SUMMARY

In accordance with an aspect, there is provided a device for separating a fluid into constituent components comprising: an inner container forming a sedimentation compartment for receiving a sample of the fluid, the inner container having an inlet port and a first aperture; an outer container for receiving the inner container and having a second aperture; a breachable diluent reservoir, wherein upon breach the internal volume of the diluent reservoir is in fluid communication with the sedimentation compartment; and at least one of the inner container and the outer container being movable between a first configuration where the outer container seals the first aperture and a second configuration wherein the first aperture and the second aperture align to form an outlet for a separated component of the sample fluid.

In some embodiments, the outer container and inner container are cylindrical or cone-shaped.

In some embodiments, the device further comprises a cap.

In some embodiments, movement of one or more of the inner container, the outer container or the cap breaches the diluent reservoir.

In some embodiments, the device further comprises indicia for indicating suitable sample size and wherein the first aperture is sized and shaped such that the volume of sample fluid plus contents of the diluent reservoir will upon settling cover a portion of the aperture while leaving an air vent at the top.

In some embodiments, the device further comprises a sample obtaining structure configured to obtain a suitable sample size and wherein the first aperture is sized and shaped such that the volume of sample fluid plus contents of the diluent reservoir will upon settling cover a portion of the aperture while leaving an air vent at the top.

In some embodiments, the device further comprises a reaction module in fluid communication with the outlet.

In some embodiments, the reaction module comprises a substrate and at least one reaction zone deposited on the substrate, wherein a reagent system specific for an analyte of interest is deposited in the at least one reaction zone.

According to an aspect, there is provided a use of the device as described herein for separating plasma from whole blood.

In some embodiments, the use of the device is for separating plasma from whole blood and for testing for an least one analyte in the separated plasma.

According to an aspect, there is provided a method for sedimentation of a volume of blood comprising: receiving a sample; diluting the sample with a diluent containing polyvinyl alcohol (PVA); and sedimenting the diluted sample.

In some embodiments, the diluent is 0.2% to 0.9% weight/volume concentration of PVA and the sample is diluted at a ratio of diluent to whole blood of 0.5:1 to 5:1.

In some embodiments, the PVA has a molecular weight between 50,000 and 250,000 Daltons.

In some embodiments, the PVA is 70% to 100% hydrolyzed.

In some embodiments, the PVA has a molecular weight of 205,000 Daltons and 88% hydrolyzed.

In some embodiments, the volume of sample is diluted using two parts diluent to one part sample, wherein the diluent is 0.2% to 0.9% weight/volume concentration of PVA having a molecular weight between 50,000 and 250,000 Daltons.

In some embodiments, the method further comprises separating sedimented cellular material from diluted plasma.

In some embodiments, the method further comprises filtering the diluted plasma.

In some embodiments, the concentration of an analyte is determined in the diluted plasma.

In some embodiments, the concentration of the analyte is determined using a reagent system specific for the analyte and wherein the reagent system is lyophilized with PVA.

In some embodiments, the concentration of the analyte is determined using a reagent system specific for the analyte and wherein the reagent system is lyophilized with a polysaccharide.

According to an aspect, there is provided a method comprising: obtaining, from an image sensor, image data representing a fluid sample diluted and reacted with reagents, the image data comprising image elements identifying instances of light intensity; correlating each of the image elements with instances of one or more reagent reactions; estimating a final concentration of a dilution analyte in the fluid sample based on the correlating; determining a dilution factor of the fluid sample by comparing the final concentration of the dilution analyte with a known initial concentration of dilution first analyte; identifying simultaneous and independent instances of a volume analyte based on the correlating; determining a relative volume of the fluid sample based on the simultaneous and independent instances of the volume analyte; and estimating a presence of a test analyte in the fluid sample based at least in part on the correlating, the dilution factor and the relative volume.

In some embodiments, the method further comprises estimating the concentration of the test analyte in the fluid sample based at least in part on the correlating, the dilution factor and the relative volume.

In some embodiments, the one or more reagent reactions includes at least one of a chemiluminescent reaction and a bioluminescent reaction.

In some embodiments, the correlating comprises comparing a measured relative intensity of the image elements with characteristic light bandwidths of the one or more reagent reactions.

In some embodiments, the method further comprises obtaining calibration data from the image sensor, wherein the estimating the presence of the test analyte in the fluid sample is based at least in part on the calibration data.

In some embodiments, the image data comprises multiple images recorded over time of reagent reactions.

In some embodiments, the multiple images capture a light decay curve of a reagent reaction.

In some embodiments, the dilution analyte contains at least one of phosphoenolpyruvate and sarcosine.

In some embodiments, the volume analyte comprises alkaline phosphatase.

In some embodiments, the identifying simultaneous and independent instances of the volume analyte based on the correlating comprises identifying image elements associated with a first . . . reaction zone, a second reaction zone and a third reaction zone of a blood separation device, wherein the second reaction zone contains a first additional amount of the volume analyte, the third reaction zone contains a second additional amount of the volume analyte, and the first reaction zone, the second reaction zone and the third reaction zone each contain equal amounts of a reagent to produce a luminescent reaction with the volume analyte.

In some embodiments, the determining a relative volume of the fluid sample based on the simultaneous and independent instances of the volume analyte comprises utilizing a method of standard addition.

In some embodiments, the test analyte is creatinine. Test analytes can also include one or more of total cholesterol, LDH cholesterol, vitamin D, glucose, TSH, or other test analytes of interest in a fluid sample such as plasma.

In some embodiments, the fluid sample is a biological sample.

In some embodiments, the fluid sample is plasma.

In some embodiments, the plasma is separated from whole blood, diluted and reacted with reagents in a separation device comprising an inner container forming a sedimentation compartment for receiving a sample of whole blood, the inner container having an inlet port and a first aperture; an outer container for receiving the inner container and having a second aperture; a breachable diluent reservoir, wherein upon breach the internal volume of the diluent reservoir is in fluid communication with the sedimentation compartment; and at least one of the inner container and the outer container being movable between a first configuration where the outer container seals the first aperture and a second configuration wherein the first aperture and the second aperture align to form an outlet for a separated component of the plasma of the whole blood.

In some embodiments, the method further comprises: receiving device information from a near field communication chip on the separation device, wherein the estimating the presence of the test analyte in the plasma is based at least in part on the device information.

According to an aspect, there is provided a mobile device comprising: an image sensor; a processor; and a memory storing processor executable instructions that when executed cause said processor to: obtain, from the image sensor, image data representing plasma separated from whole blood, diluted, and reacted with reagents, the image data comprising image elements identifying instances of light intensity; correlate each of the image elements with instances of one or more reagent reactions to generate a correlation; estimate a final concentration of a dilution analyte in the plasma based at least in part on the correlation; determine a dilution factor of the plasma by comparing the final concentration of the dilution analyte with a known initial concentration of dilution analyte; identify simultaneous and independent instances of a volume analyte based at least in part on the correlation; determine a relative volume of the plasma based at least in part on the simultaneous and independent instances of the volume analyte; and estimate a presence of a test analyte in the plasma based at least in part on the correlation, the dilution factor and the relative volume.

According to an aspect, there is provided a method for determining the amount of an analyte of interest in an unknown quantity of sample comprising: providing three reaction channels each containing a reagent that reacts with the analyte to produce either a first detectable signal proportional to the amount of the analyte in the reaction channel or a reaction product that can be further reacted to produce the first detectable signal proportional to the amount of the analyte in the reaction channel, the first reaction channel containing a known first quantity of the analyte of interest n, the second reaction channel containing a known second quantity of the analyte of interest m, wherein m is different than n, and the third reaction channel containing a known third quantity of the analyte of interest o, wherein o≠m or n, depositing a volume of the sample in each of the reaction channels; measuring the first detectable signal produced in each reaction channel; and determining the amount of analyte in the unknown sample based on the method of standard addition.

In some embodiments, n=0.

In some embodiments, the method further comprises determining a dilution factor DF for the sample by diluting the sample with a diluent that contains a known concentration X of a control analyte not present in the sample; providing three dilution factor channels each containing a reagent that reacts with the control analyte to produce either a second detectable signal proportional to the amount of the control analyte in the dilution factor channel or a reaction product that can be further reacted to produce the second detectable signal proportional to the amount of the control analyte in the dilution factor channel, the first dilution factor channel containing a known first quantity of the control analyte p, the second dilution factor channel containing a known second quantity of the control analyte q, wherein p is different than q, and the third dilution factor channel containing a known third quantity of the control analyte r, wherein r≠p or q, depositing a volume of the sample in each of the dilution factor channels; measuring the second detectable signal produced in each dilution factor channel; and determining the concentration Xr of the control analyte in the diluted sample at the reaction zone in the first dilution factor channel; determining DF, wherein DF=[X]/[Xr].

In some embodiments, the reagents and the first, second and third quantities of analyte are lyophilized.

In some embodiments, the sample is blood plasma.

Many further features and combinations thereof concerning the present improvements will appear to those skilled in the art following a reading of the instant disclosure.

DESCRIPTION OF THE DRAWINGS

FIG. 1 is a front perspective view of a fluid separation device according to one embodiment.

FIG. 2 is a rear perspective view of the device of FIG. 1.

FIG. 3 is a top plan view of the device of FIG. 1.

FIG. 4 is a front elevation view of the device of FIG. 1.

FIG. 5 is a side elevation view of the device of FIG. 1.

FIG. 20 is a front perspective view of an inner container according to one embodiment.

FIG. 21 is a rear perspective view of the inner container of FIG. 20.

FIG. 22 is a top plan view of the inner container of FIG. 20.

FIG. 23 shows a perspective view of a cap spacer according to an embodiment.

FIGS. 24A and 24B show front and rear perspective views of an alignment tab according to an embodiment.

DETAILED DESCRIPTION

Figure 6:
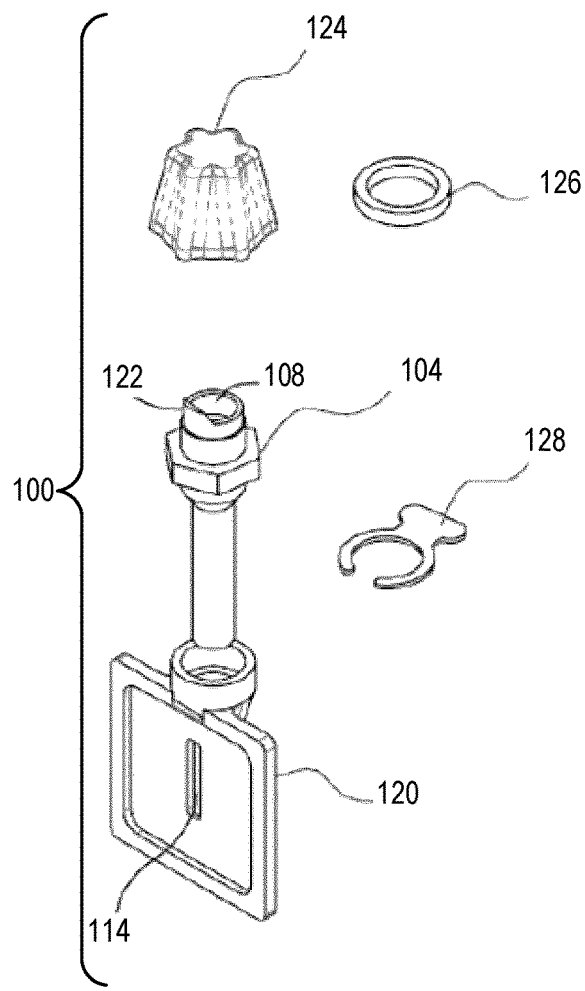
FIG. 6 is an front exploded perspective view of the device of FIG. 1.

In some embodiments, there is provided a separation device 100 that is a passive, microfluidic, disposable device that accepts whole blood, separates out the blood plasma, distributes the plasma to a biochemistry test platform that can perform multiple, simultaneous, varied tests using test methodologies that can include photometric, chemiluminescence, bioluminescence, electro chemiluminescence, and fluorescence measurement methods. The use of chemiluminescence and bioluminescence (CB) methods which may be typically 10,000-100,000 times more analytically sensitive than photometric and a 1,000 times more than fluorescent methods are described herein. In some embodiments, the separation device 100 utilizes a mobile device (e.g., a smartphone) as the optical imager, measurement tool, and analyser. This can provide a fast, accurate point of care device that does not require certain special skills or experience to use.

One approach to capillary-based (micro-volume) testing is to passively separate plasma through use of size-exclusion filter material. Cellular matter in blood has a size whereby filter material with a pore size of about 2-4 um in diameter will prevent the cellular matter from transiting-getting stuck in the filter material while plasma can flow through. Filtration typically takes 10 minutes or longer. There are issues with this approach. For example, there is a potential to rupture the cellular material which will cause hemolysis and contaminate the plasma, invalidating most tests. Thus pressure cannot be used to speed up filtering. As another example, there is a potential that some cellular matter will transit the filter, again causing problems with downstream testing. Thus filter quality must be high. As another example, filter material is prone to clogging as it is in its nature to hold back the cellular material. If the surface area of the filter is insufficient, the filter will eventually clog and thereby prevent any further flow of plasma.

As the surface area is increased to prevent clogging, another issue becomes more pronounced: hold-back volume. All filters are made of a material that has openings to allow fluid to transit. The size of these openings (average pore size) is controlled. For any filter, the total volume of the openings is called void volume and typically after filtration, the void volume contains the filtride and some remaining filtrate. This hold-back affects 'yield' i.e. the percentage of filtrate that is recovered after filtration over the amount that was actually available. In small filtrations such as from a few drops of blood the hold-back volume can be significant and yields therefore are typically less than 60%. For a person with a hematocrit 50%, 100 ul of blood (about 2 drops) will typically yield only about 30 ul of plasma if there is no clogging. In one example of a combination of passive sedimentation with filtration [Membrane-based, sedimentation-assisted plasma separator for point-of-care applications Anal Chem. 2013 Nov. 5; 85 (21): 10463-10470. Changchun Liu, Michael Mauk, Robert Gross, Frederic D. Bushman, Paul H. Edelstein, Ronald G. Collman, Haim H. Bau], in about 7 minutes the authors recovered about 275 ul from about 2 ml of whole blood, or a 30% yield. With such little amounts of plasma, it becomes very difficult to transfer and work with the volume for testing purposes.

Due to these challenges, passive techniques using filters typically are suitable for single tests but not panels due to low yield and reduced volumes.

Separation Device

In an embodiment, device 100 includes a fluid separation component. The separation device 100 may be embodied in the form of a convenient, mobile apparatus, for example.

Fluid separation component 102 is adapted for the separation of fluid into constituent components. Fluid separation component 102 can be adapted for the removal of one or more of the separated components from the remainder of the fluid. In a preferred embodiment, the separated and removed fluid is subjected to further analytical testing within device 100. In some embodiments, the fluid separation component 102 comprises an inner container 104 forming a sedimentation compartment 106 for receiving a sample of the fluid, the inner container 104 having a sample receiving inlet port 108 and a first aperture 110; an outer container 112 for receiving the inner container 104 and having a second aperture 114; and a frangible diluent reservoir 116 wherein upon breach, the internal volume of the diluent reservoir 116 is in fluid communication with the sedimentation compartment 106; at least one of the inner container 104 and the outer container 112 being movable between a first configuration where the outer container 112 seals the first aperture 110 and a second configuration wherein the first aperture 110 and the second aperture 114 align to form an outlet 118 for a separated component of the sample fluid.

In one embodiment, device 100 further includes a reaction module 120 in fluid communication with the outlet 118 for receiving the separated component of the fluid sample.

As described above, the fluid separation component 102 suitably comprises an inner container 104 forming a sedimentation compartment 106 for receiving a sample of the fluid 107. A sample 107 is introduced into the sedimentation compartment 106 via the sample receiving inlet port 108 and the fluid separates into constituent components within the sedimentation compartment 106 due to gravitational forces. Previously, careful technique would be required to separate constituent components of a fluid allowed to separate under gravitational forces. Device 100 may provide a simple means for separating a component from the separated sample which requires limited manual skill.

The inner container 104 and the outer container 112 are configured and dimensioned to allow transition from a first position to a second position relative to each other. In one embodiment, the inner container 104 can be rotated within the outer container 112 to align the first aperture 110 and the second aperture 114 to form the outlet 118. In this embodiment, the outer container 112 and inner container 104 may be e.g. concentric cylinders or cones. In another embodiment, the inner container 104 may be telescopically received within the outer container, such that it is slidable from a first position in which the outer container 112 seals the first aperture 110 to a second configuration wherein the first aperture 110 and the second aperture 114 align to form an outlet 118 e.g. the outer container 112 may be a tubular structure with a slot on a wall distal the sample receiving port 108 and the inner container 104 may move from a first position in which it is only partially received within the outer container 112 and the first aperture 110 is aligned with the solid wall of a proximal portion of the outer container 112 to a second position wherein the first aperture 110 is aligned with the slot. The cross-sectional shape of the tube in this embodiment is not particularly restricted and could be e.g. a circular, square or triangle. In one embodiment, the outer container 112 and inner containers are concentric open-topped cylinders. In the first position, the first aperture 110 (of the inner container) and the second aperture 114 (of the outer container) are not aligned and the outer container 112 seals the first aperture 110 to prevent egress of fluid from the sedimentation compartment. In the second position, the first aperture 110 and the second aperture 114 are aligned creating an outlet 118 for egress of fluid from the sedimentation compartment 106. Suitably the apertures (110, 114) are sized and/or positioned to limit egress to a component of the fluid, while preventing egress of the remainder of the diluted fluid sample. In one embodiment, the apertures (110, 114) are slots. It one embodiment, the outlet 118 is positioned so that it will be positioned above a sedimented component of the fluid after separation. In one embodiment, the sample is whole blood and the cellular components are sedimented beneath the outlet 118, while plasma passes though the outlet 118.

While the device has been described here with a single first aperture 110 and a single second aperture 114, the inner container 104 may have a plurality of apertures alignable with a plurality of apertures on the outer container 112. These apertures may be in close proximity to each other or they may be separated from each other. Apertures positioned separately from each other may nevertheless be positioned such that the same component will egress from the outlets formed thereby e.g. the outlets may be positioned at the same level vertically on the device but may be on opposite sides of the sedimentation compartment 106 and may fluidly connect to separate reaction structures. In another embodiment, the separated outlets may be positioned such that different components of a separated fluid will pass through the outlets once the inner container 104 and outer container 112 are brought into alignment, i.e. the outlets may be positioned at different levels within the sedimentation compartment 106.

The first and second apertures (110, 114) are suitably sized and/or positioned so that after sedimentation, the sedimented sample will not fully occlude the outlet 118 when the first and second apertures (110, 114) are brought into alignment. Having the outlet 118 only partially occluded by the sedimented sample permits air flow through the outlet 118 facilitating egress of fluid from the sedimentation compartment 106.

As will be apparent to a person of skill in the art, the preferred dimensions of the outlet 118 (and, accordingly, the preferred dimensions of the first and second apertures 110, 114) will depend on the volume sample and ascertaining the same will be within the purview of a person of skill in the art. In one embodiment, the sample is of whole blood sample and the device operates to separate plasma for testing. The separation device as described herein can efficiently separate the blood plasma from as little as 1 drop of blood. The device may operate efficiently to separate about 50 μl up to a few mL of whole blood. The blood is suitably diluted at a ratio of between 0.5 part diluent to 1 part whole blood and 5 parts diluent to 1 part whole blood with diluent from the diluent reservoir 116 thereby yielding a suitable sample for testing. In this embodiment, the first and second apertures 110, 114 suitably have a length of between 5 and 20 mm, preferably 3 to 5 mm.

The length of the slot is suitably determined based on the volume of liquid expected to be available to pour off and diameter of the inner sphere. The length of the slot should be higher than the fluid height to ensure that there is no vacuum plug caused if the fluid is above the top of the slot. For a cylinder, for example, volume is $V=\pi r^2 h$ where h is the length, so the slot length should be about 2 mm or greater than the volume of the fluid divided by Pi times the square of the radius. The width of the slot needs to be wide enough to overcome any surface tension forces of the liquid in question. Typically any width greater than 3 mm is viable. The maximum width is mostly governed by the cylinder circumference and could reasonably be up to 10 mm wide.

In one embodiment, device 100 includes a sample receiving well fluidly connected to the sample receiving port 108 and for receiving a sample from a user. The sample receiving well may be sized so that when filled it provides an appropriate sample size based on the size and/or position of the outlet 118. Alternatively, the well may include indicia to show a user when sufficient sample has been introduced into the well. In another embodiment, the sample receiving well may include a sample obtaining structure 122 such as a sharp scoop for obtaining a blood sample from a subject, and the sample obtaining structure 122 may be proportioned to obtain an appropriate sample size.

The outer container 112 is suitably configured and dimensioned to receive the inner container 104 to provide a snug, sealing, or tight fit that prevents or minimizes egress of sample from the sedimentation compartment 106, both during alignment or partial alignment of the first and second apertures 110, 114 (i.e. such that fluid passing through the outlet 118 does not leak into the volume between the inner and the outer containers) or when the apertures are not aligned. Suitably, one or both of the inner container 104 and outer container 112 include feature(s) that prevent(s) further movement (e.g. sliding or rotation) once the first aperture 110 and the second aperture 114 are brought into alignment. For example, in one embodiment, the inner container 104 and outer container 112 have external tabs (not shown) that abut when rotated such that the apertures 110 and 114 align.

In some embodiments, one or more portions of the inside surface of the inner container 104 are exposed and/or the inside volume of the inner container 104 is in fluid communication with the inside volume of the outer container 112 when the first aperture 110 and the second aperture 114 are not in alignment. In this situation, contents contained in the inner container 104 may be prevented from exiting the inner container 104 by virtue of gravity and/or the position, dimension, and/or configuration of the inner container, the outer container, and/or a component of the separation device 100, for example.

The sample contained within the sedimentation compartment 106 may be prevented by a physical barrier e.g. a one way valve from exiting the sedimentation compartment 106 other than through the outlet 118. In one embodiment, the device 100 may simply be oriented by the user so that the sample 107 is retained within the sedimentation compartment 106 and egress is only through the outlet 118. In one embodiment, separation device 100 includes a base station 134 for receiving the fluid separation component 102, which in one embodiment, is configured to ensure proper orientation of the fluid separation component 102 for sedimentation. In one embodiment, the inner container 104 is sealed by a cap 124 that covers the sample receiving port 108 and which may be manually applied by a user. In one embodiment, the cap 124 is a threaded screw top cap, which can be screwed onto a cooperating threaded surface of the inner container.

The sample 107 is suitably combined with a diluent 109. The diluent 109 is suitably housed in a diluent reservoir 116. While the reservoir is referred to as a diluent reservoir, in one embodiment, the contents of the reservoir are not specifically restricted. The reservoir 116 may contain one or more components that can aid or enable separation or sedimentation of a sample. In one embodiment, a sedimentation accelerator aids in the sedimentation and separation of whole blood; in one embodiment, pectin and/or polyvinyl alcohol (PVA). As another example, a component in a diluent reservoir 116 can be a solid e.g. a powder. However, in a preferred embodiment, the diluent will be a liquid. In some embodiments, diluent 109 is contained in a cylinder such as inner container 104.

In some embodiments, diluent 109 includes a buffer such as one or more of a phosphate buffered saline (PBS) at physiological pH (i.e., 7.4) and a tris(hydroxymethyl)aminomethane (TRIS) buffered saline at physiological pH (i.e., 7.4). In an example, a buffer of diluent 109 can have a pH at or between 7.5 and 9. Diluent 109 can also include a sedimentation accelerator, such as PVA as described above, and other constituents such as alkaline phosphatase.

Breach of the diluent reservoir 116 enables its contents to combine with the sample 107. In another embodiment, the inner container 104 is sealable by a cap 124 and a cooperating structure on one of the inner or outer container 112 pierces the diluent reservoir 116 when the inner container 104 is sealed by the cap. Other configurations enabling breach of the diluent reservoir 116 are possible, e.g. the diluent reservoir 116 may be a blister pack which may be depressed or squeezed by the user to release the contents into the sample receiving well or sedimentation compartment 106.

The configuration and/or dimensions of each container can be such that when the apertures of the inner container 104 and the outer container 112 are brought into registration, the diluent reservoir 116 is breached facilitating separation of components in a sample in the sedimentation compartment 106, suitably in a ratio of diluent to whole blood of 0.5:1 to 5:1, with a preferred ratio being 2:1.

Figure 8:
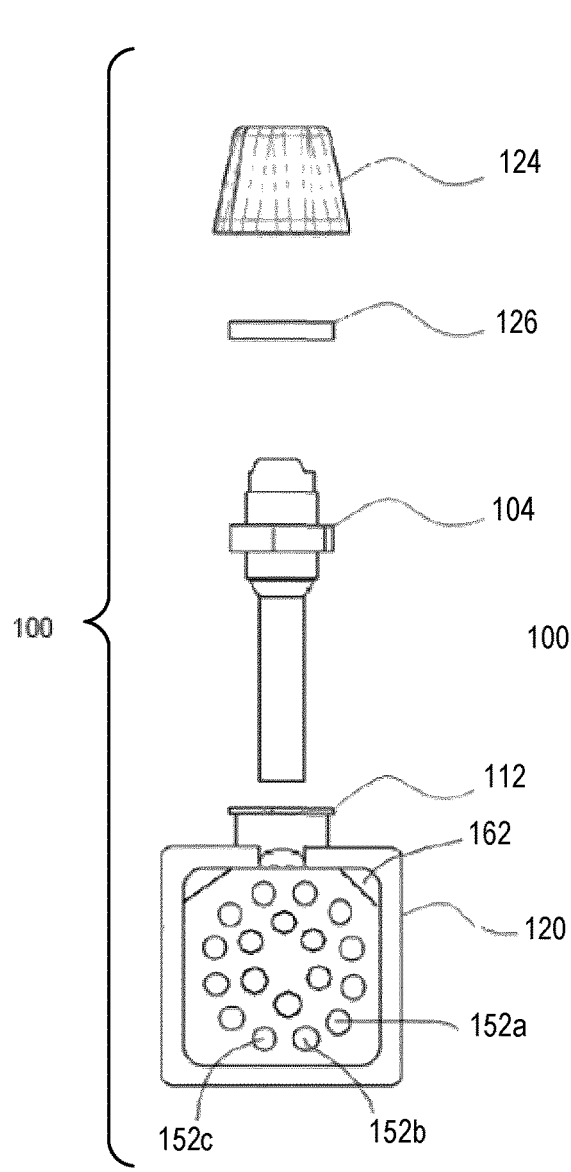
FIG. 8 is an exploded front elevation view of the device of FIG. 1 including a reaction module according to one embodiment.
Figure 9:
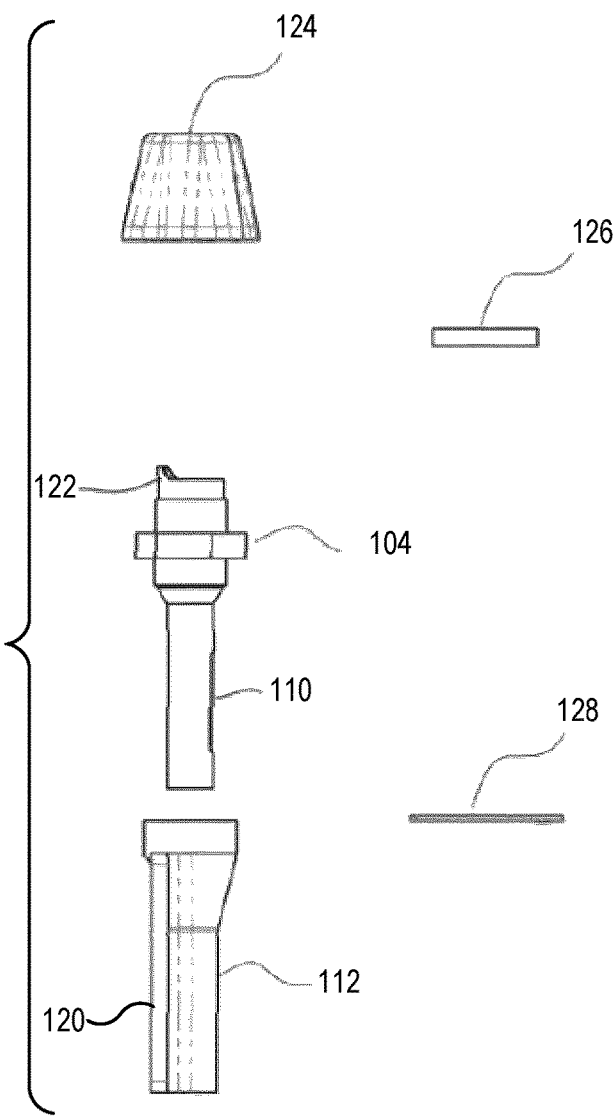
FIG. 9 is an exploded side elevation view of the device of FIG. 1.

As shown for example in FIG. 8, device 100 may include a reaction module 120. The outlet 118 created upon alignment of the first aperture 110 with the second aperture 114 of the inner container 104 and the outer container 112, respectively, is in fluid communication with the reaction module 120. FIG. 9 is an exploded side elevation view of device 100.

Figure 7:
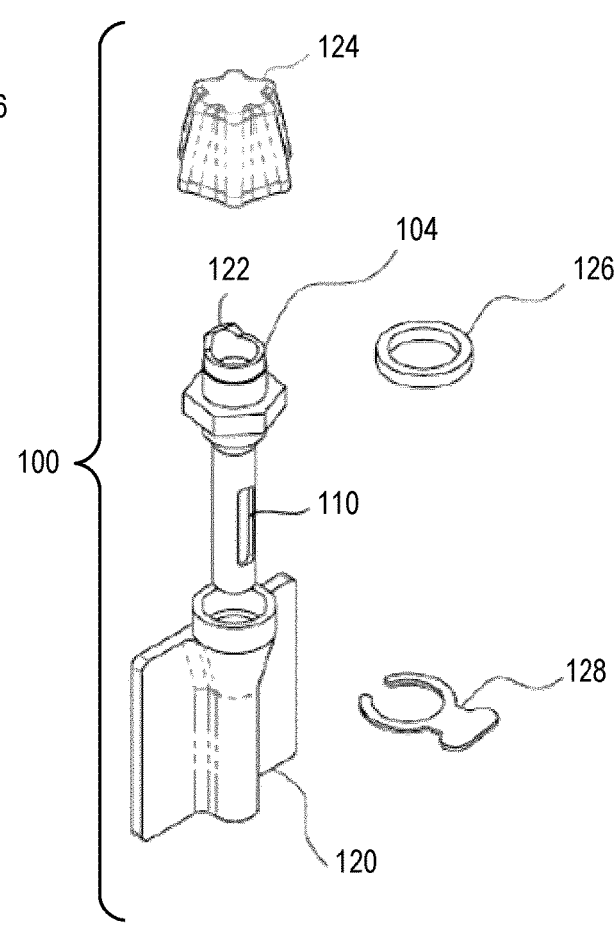
FIG. 7 is a rear exploded perspective view of the device of FIG. 1.

Referring to the figures, in some embodiments, device 100 is a single passive, device composed of the inner container shown in FIG. 1 as an inner cylinder, the outer container 112, here shown as an outer cylinder, a cap 124, a reaction module 120, a cap spacer 126, an alignment tab 128, and a mixing aid here shown as a small ball bearing 130. FIG. 2 is a rear perspective view of device 100, FIG. 3 is a top plan view of device 100, FIG. 4 is a front elevation view of device 100, FIG. 5 is a side elevation view of device 100, FIG. 6 is an front exploded perspective view of device 100, and FIG. 7 is a rear exploded perspective view of device 100, in accordance with an embodiment. Further components and configurations of device 100 are described below according to some embodiments. While reference is made in the discussion below to the inner and outer cylinders as shown in the figures, this discussion is applicable to devices having inner and outer containers of different geometry. Similarly, the apertures can be of a different geometry than as shown in the figures and different arrangements of the apertures are possible as described above.

In some embodiments, the device 100 comprises two narrow, thin walled, cylinders, each open at the top but closed at the bottom and with inner container 104 being inside outer container 112 with the inner container 104 outer diameter being just slightly smaller than the outer container 112 inner diameter. The open top of the inner container 104 acts as the inlet port 108, however, other configuration are possible for example, the inlet may be an aperture in a closed top. In one embodiment, the inner container 104 is taller than the outer container 112 and is enlarged at the top in smooth taper to better allow blood droplet collection and threaded to allow for a screw cap. Both cylinders have a vertical aperture (or slot) on the cylinder side wall so that if turned about its long, vertical axis, the inner slot will line up with the outer slot so that any liquid contained in the inner container 104 will flow out of the inner container 104 and also out of the outer container 112. If turned out of alignment (initial condition) any liquid in the inner container 104 will be contained in inner container 104. The preferred embodiment has such fine tolerance that the space between the cylinders will not permit fluid to leak out from the first aperture 110 in the inner container 104. In another embodiment, a sealing material coats the exterior of the inner container 104, which helps prevent leaks but also facilitates movement of the inner container relative to the outer container 112. In the case of blood separation, suitably the sealing material is non-reactive with blood and non-hydrophilic such as silicon grease. In some embodiments, the inner container 104 and outer container 112 are each configured and/or configured in relation to each other to form a tight seal such that contents of inner container 104 is maintained within inner container 104 until the slots are brought into alignment.

The thicknesses of inner container 104 and outer container 112 should be minimized to limit the amount of liquid held back in the volume governed by thickness of each aperture 110, 114 and, while maintaining sufficient rigidity to prevent or minimize deformation, which can result in leakage. Suitable materials can include e.g. metals such as aluminum but preferred materials are relatively neutral hydrophobic/hydrophilic polymers that do not react with blood such as polyethylene, polypropylene, and polyethylene terephthalate. The inner and outer containers 104 and 112, and in particular, the inner wall(s) of the inner container 104 should be relatively inert smooth surfaces and be neither significantly hydrophobic nor hydrophilic, which will prevent the cells and other sample components from adhering to the walls.

FIG. 20 is a front perspective view of inner container 104, FIG. 21 is a rear perspective view of inner container 104, and FIG. 22 is a top plan view of inner container 104, in an embodiment.

In one embodiment, both cylinders have threading that allows the inner container 104 to be screwed into the outer container 112 at the top of the outer container 112 to secure the cylinders in a connected arrangement and so as to enable initial slot misalignment and subsequent alignment (preferably by manual turning of the inner container 104) while keeping the inner container 104 and outer container 112 vertically aligned. The threads are designed to maintain the close tolerance on the cylinder diameter. The first aperture 110 in the inner container 104 is raised above the bottom to such a height so as most of the cellular matter in blood, after sedimentation, along with the ball bearing, will be below the aperture. There is a thicker ring area (abutment) on the outside near the top of inner container 104 that acts as an abutment to stop the clockwise screwing once the slots line up. Other structures may provide analogous abutment or structure to facilitate alignment (or misalignment) between inner container 104 and outer container 112 or to otherwise facilitate one or more particular configurations of inner container 104 in relation to outer container 112.

In some embodiments, the top of inner container 104 includes a sample obtaining structure 122, here shown as a "scoop" protuberance which better allows it to scoop or collect blood drops. This scoop can also to act as a bayonet to breach the diluent reservoir 116 in the cap 124. The protuberance may e.g. cut a plastic seal releasing the contents of the diluent reservoir 116. The inner container 104 may be configured to facilitate sample collection, such as blood drops, and/or mixing of sample with diluent.

Figure 10A:
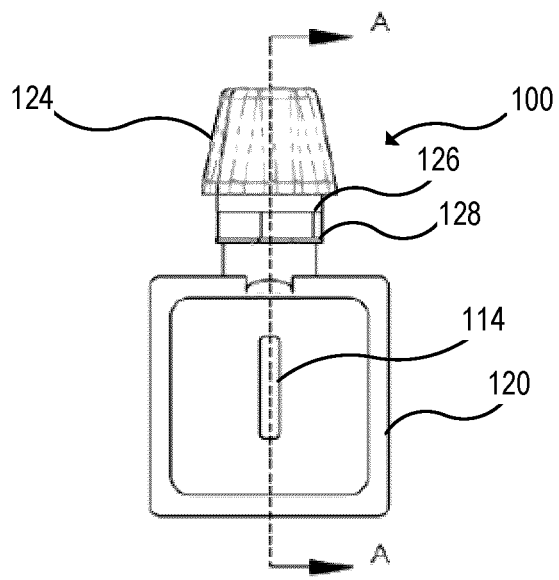
FIG. 10A is a front elevation view of a device according to one embodiment.
Figure 10B:
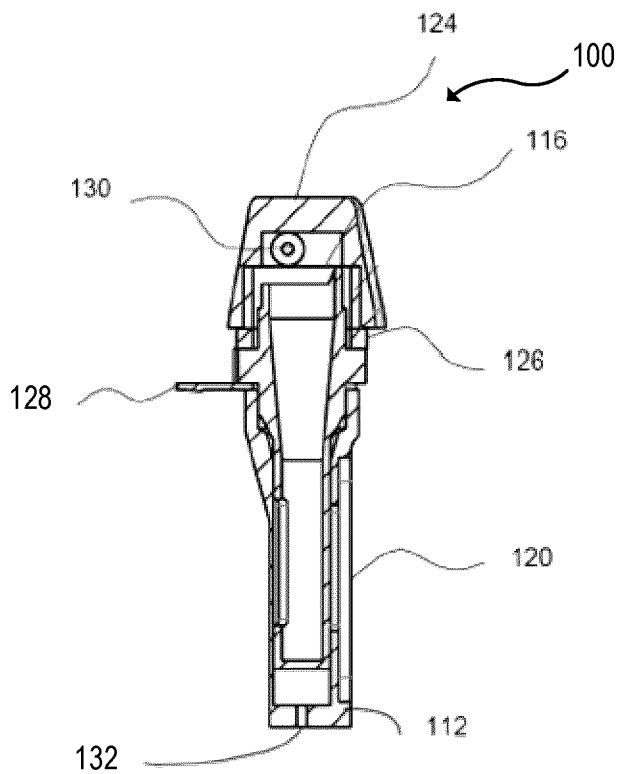
FIG. 10B is a cross sectional view along the line A-A of FIG. 10A.

FIG. 10A is a front elevation view of device 100 according to one embodiment. FIG. 10B is a cross sectional view along the line A-A of FIG. 10A.

In some embodiments, there is a small air vent 132 (FIG. 10B) near or in the bottom of outer container 112 that allows air to exit when inner container 104 is screwed down into outer container 112.

In some embodiments, instead of threading that holds together and aligns inner container 104 and outer container 112, there is a thin protruding ring (not shown) on the outside, near the top, of inner container 104 which can be pressed into a thin depressed ring on the inside, near the top, of outer container 112 to hold the cylinders in place but allow for easy turning of the inner container 104 in outer container 112. In this embodiment, there are protruding tabs on the outside of both the inner container and outer container 112 which restrict the turning of inner container 104 between 180 degree misalignment to perfect alignment of the apertures in inner container 104 and outer container 112. Other configurations are possible, such as a snap fit arrangement.

Figures 11A, 11B:
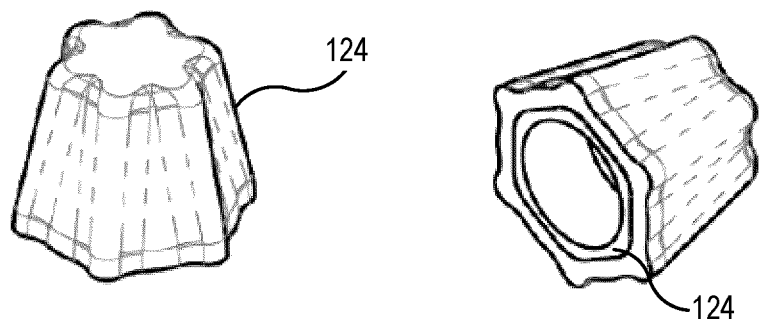
FIG. 11A is a top perspective view of a cap according to one embodiment.
FIG. 11B is a bottom perspective view of the cap of FIG. 11A.
Figure 11C:
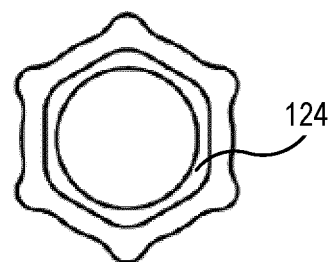
FIG. 11C is a bottom plan view of the cap of FIG. 11A.
Figures 12A, 12B:
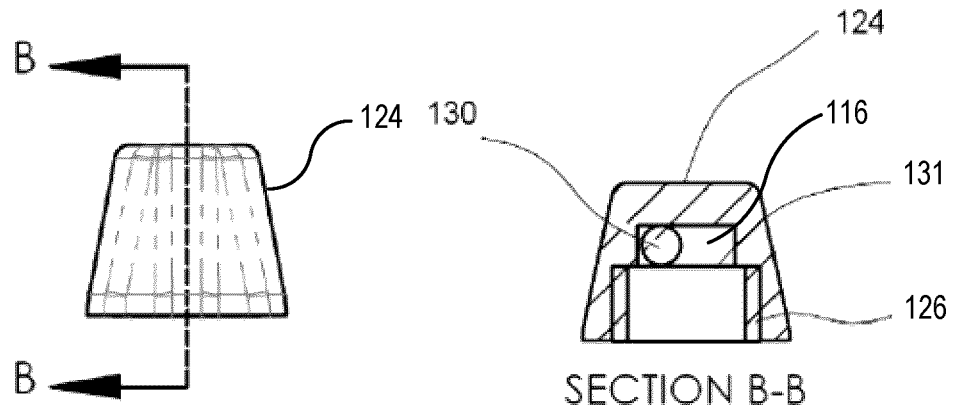
FIG. 12A is a side elevation view of a cap according to one embodiment.
FIG. 12B is a cross-sectional view along the line B-B of FIG. 12A.

FIG. 11A is a top perspective view of cap 124 according to one embodiment. FIG. 11B is a bottom perspective view of cap 124, and FIG. 11C is a bottom plan view of cap 124. FIG. 12A is a side elevation view of cap 124 according to one embodiment, and FIG. 12B is a cross-sectional view along the line B-B of FIG. 12A.

In some embodiments, screw cap 124 contains an inner diluent reservoir 116, as shown for example in FIG. 12B, enclosed inside and suitably near the top of the cap 124. In the case of plasma collection from blood droplets, the diluent reservoir 116 suitably contains 1-400 ul of a solution or diluent mix. The opening of cap 124 can include a thin plastic or mylar seal 131 that holds the diluent mix in place but is designed to be easily cut, releasing the liquid. This can be recessed into the cap 124 opening so that initially the cap 124 can be screwed onto inner container 104 without cutting the seal 131.

In some embodiments, the reservoir also contains a mixing aid, suitably a small weighted ball bearing 130 made of a non-reactive metal alloy such as brass that will enhance mixing of the sample 107 and diluent 109 once released. Preferably, this metal ball bearing 130 is small enough to easily fit in the inner container 104, is much more dense than the sample and diluent, but does not take up much volume. The mixing aid facilitates mixing of the diluent and the sample such as whole blood thereby accelerating the separation process. Mixing may suitably be effected by gentle manual agitation or "rocking" of the container, which in the presence of the ball bearing 130 is sufficient to enable adequate mixing. In the case of separation of plasma from whole blood, this arrangement avoids more aggressive techniques which can break the cells thereby yielding a more contaminated plasma product.

In some embodiments, there is a small air or expansion vent (not shown) at the top of the cap 124 to enable freezing of the device 100 and diluent 109.

In some embodiments, a cap spacer 126 shown in an embodiment in FIG. 23, in one embodiment a small plastic, cylinder fits loosely over inner container 104 at the top and sits atop the abutment and acts as a spacer so when in place, the cap 124 cannot be screwed on so far as to permit the scoop (or other analogous feature) to break the seal, but when easily removed after cap 124 removal and before screwing the cap 124 back on, the scoop (or other analogous feature) can now break the seal and release the diluent into inner container 104.

In some embodiments, there is an alignment tab 128 shown in an embodiment in FIGS. 24A and 24B, here shown as a pull-removable tab, attached below the abutment that prevents the clockwise turning of inner container 104 in outer container 112 and keeps the aperture 110 in inner container 104 180 degrees out of horizontal alignment with the aperture 114 in outer container 112, but when pulled to remove, will allow further turning (suitably a further ½ clockwise turn) of inner container 104 so that the apertures in inner container 104 and outer container 112 come into horizontal and vertical alignment.

For use in the separation of blood plasma, suitably the above-described components of device 100 are fabricated using material that is non-reactive with blood and does not alter the constituent concentrations of plasma. An example of this type of material is polypropylene. In one embodiment, some or all of the above-described components of fluid separation component 102, other than ball bearing 130, are manufactured from a plastic, suitably polypropylene.

In some embodiments, one or more of these components are fabricated using material that may affect blood or constituent concentrations to a level that may be mitigated, accounted for, and/or tolerated by device 100 or a processor that analyzes an output of same.

In some embodiments, the outlet 118 leads to a collection chamber or vessel (not shown) for receiving the separated component of the fluid. In one embodiment, this collection chamber or vessel is releasably connected to the remainder of device 100. In another embodiment, outlet 118 is configured for connection to another device for withdrawing the separated component of the fluid e.g. a syringe.

In other embodiments, the outlet 118 is fluidly connected to a reaction module 120.

Reaction Module

In one embodiment, a reaction module 120 or parts thereof may be connected to the remainder of device 100 e.g. by a snap fit connection. As will be apparent, this can enable a user to select a module for use with separation device 100. Further, this enables separation device 100 and reaction module 120 to be stored and transported separately, which can be beneficial as the storage conditions for reaction module 120 may need to be more closely controlled based on the analytes present in the reaction zones described below.

Figure 13:
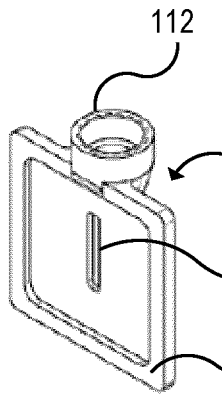
FIG. 13 is a front perspective view of an outer container and attached support structure of a reaction module according to one embodiment.
Figure 14:
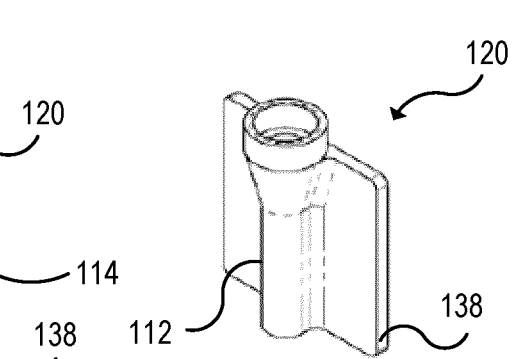
FIG. 14 is a rear perspective view of the outer container and attached support structure of reaction module of FIG. 13.
Figure 15:
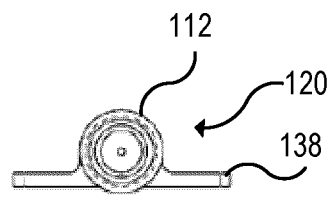
FIG. 15 is a top plan view of the outer container and attached support structure of reaction module of FIG. 13.
Figure 16:
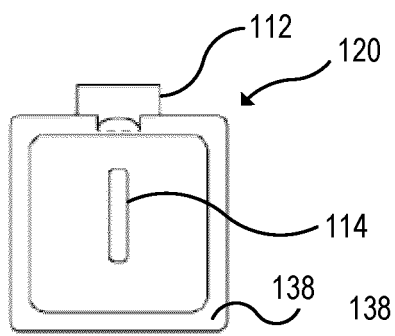
FIG. 16 is a front elevation view of the outer container and attached support structure of reaction module of FIG. 13.
Figure 17:
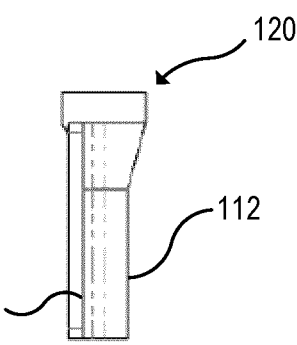
FIG. 17 is a side elevation view of the outer container and attached support structure of reaction module of FIG. 13.
Figure 18:
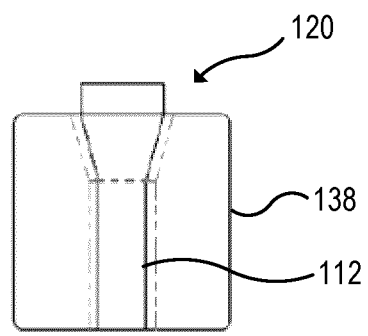
FIG. 18 is a rear elevation view of the outer container and attached support structure of reaction module of FIG. 13.
Figure 19:
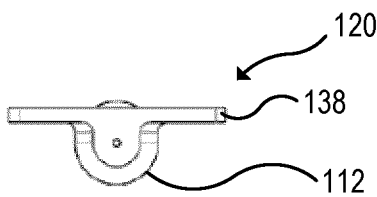
FIG. 19 is a bottom plan view of the outer container and attached support structure of reaction module of FIG. 13.

FIG. 13 is a front perspective view of outer container 112 and attached support structure 138 of reaction module 120 according to one embodiment. FIG. 14 is a rear perspective view of the outer container 112 and attached support structure 138 of reaction module 120. FIG. 15 is a top plan view of outer container 112 and attached support structure 138 of reaction module 120. FIG. 16 is a front elevation view of outer container 112 and attached support structure 138 of reaction module 120. FIG. 17 is a side elevation view of outer container 112 and attached support structure 138 of reaction module 120. FIG. 18 is a rear elevation view of outer container 112 and attached support structure 138 of reaction module 120. FIG. 19 is a bottom plan view of outer container 112 and attached support structure 138 of reaction module 120.

The reaction module 120 includes a support structure 138 for supporting a sample receiving structure 140 that includes at least one reaction zone having deposited thereon or therein a reagent system specific for an analyte of interest which upon interaction with the analyte produces a signal indicative of an assay value of the analyte of interest. In a preferred embodiment, the sample receiving structure 140 has a plurality of reaction zones 152*a*, 152*b*, 152*c*, 153*a*, 153*b*, 153*c* deposited thereon or therein as described further below.

While in one embodiment, the size and shape of the support structure 138 is not particularly restricted, in one embodiment, the support structure 138 is a flat platform capable of receiving thereon the sample receiving structure 140. In one embodiment, the sample receiving structure 140 may be attached to the support structure by a user e.g. by snap fit. In one embodiment, the support structure 138 is integrally formed with outer container 112, while in another embodiment, the support structure 138 is releasably connectable to the outer container 112.

As described above, the sample 107 may be whole blood and, upon sedimentation of the sample and alignment of the first aperture 110 with the second aperture 114, plasma is able to exit the inner container 104 through the outlet 118 created by the alignment of the first and second apertures (110,114), which is in fluid communication with the reaction module 120.

The reaction module 120 includes means for further apportioning the separated fluid component into different reaction zones 152a, 152b, 152c, 153a, 153b, 153c which can include channels or pores or portions of absorbent layers that allow for an appropriate level of isolation for a reaction.

The reaction zones 152a, 152b, 152b, 153a, 153b, 153c can include a reagent, analyte diluent, reactive indicator, sample or portion thereof, which may be immobilized. Immobilization can be effected by drying reagent(s) onto surface(s) of the reaction zones such as absorbent layers. In one embodiment, reagents are combined with PVA prior to deposition on a reaction zone surface.

The reaction module 120 can be an integrated square vertical platform. The reaction platform may be separately constructed and connectable to the separation device 100. Alternatively, the platform may be integrally formed with one or more parts of separation device 100 and, in particular, may be integrally formed with the outer container 112. Other shapes and configurations of the reaction module 120 are possible.

Figure 25:
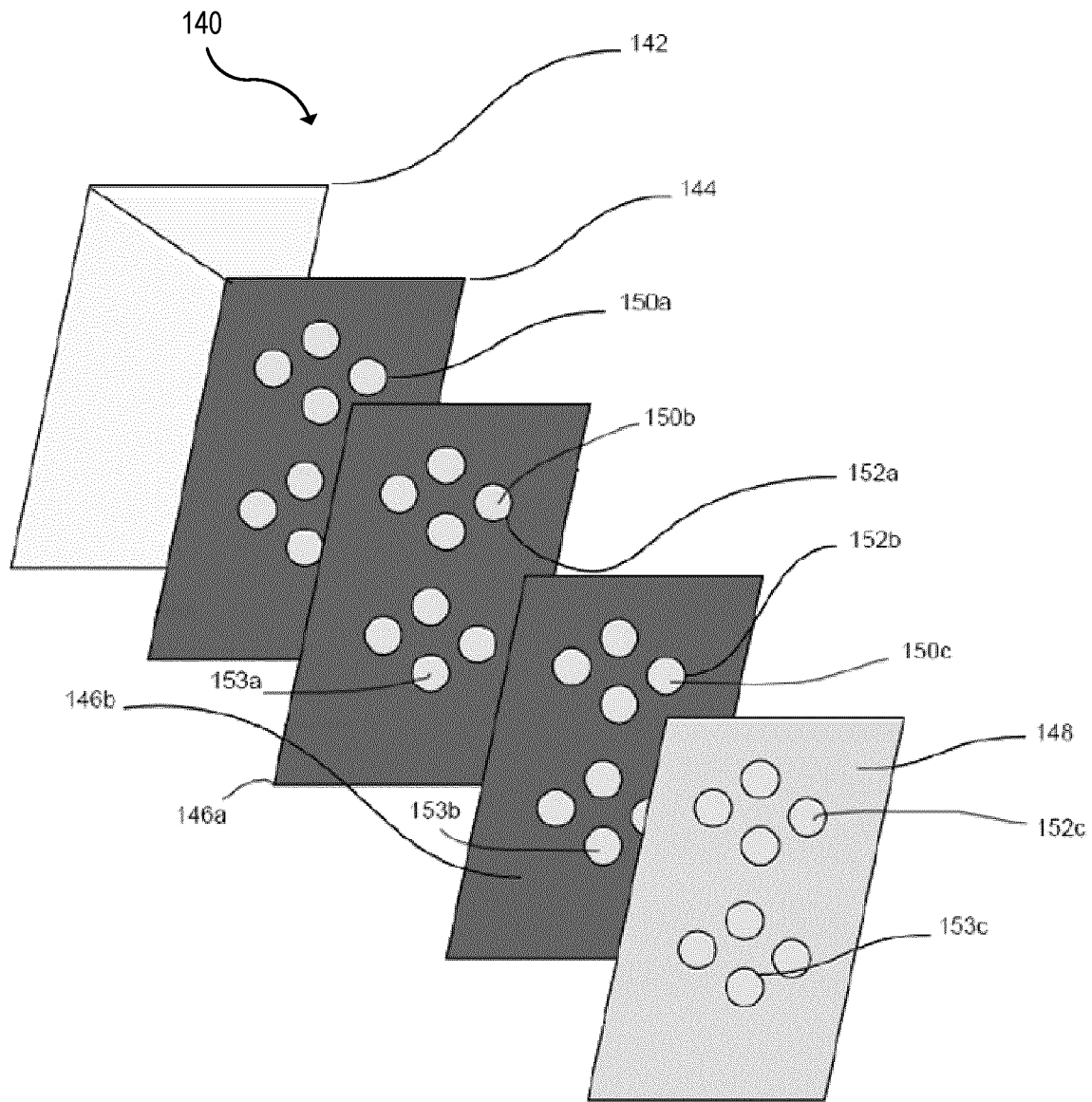
FIG. 25 is an exploded schematic view of a sample receiving structure of a reaction module according to one embodiment.

The receiving structure 140 can include one or more (preferably a plurality) of channels which serve to channel sample (e.g. separated plasma sample) to individual reaction zones (in the case of FIG. 25 channel 150 is shown by reference numerals 150a, 150b, 150c, the channel being in relation to reaction zones 152a, 152b and 152c). While the term "channel" is used, it will be understood that the particular shape or size of the channel is not particularly restricted, as long as the relevant structure provides the function of apportioning and transporting sample to individual reaction zones 152a, 152b, 152c. Further, the channels 150a, 150b, 150c, may be open channels i.e. apertures through which the sample passes or the channels may be formed, whether partially or completely, of hydrophilic materials that act as wicks to transport the sample to the reaction zones 152a, 152b, 152c. Further, a channel may pass through a plurality of reaction zones positioned in series (as shown in FIG. 25) i.e. the same apportioned sample can pass through a first reaction zone and a second reaction zone before being deposited on a readout layer in a position aligned with the first and second reaction zones.

In some embodiments, receiving structure 140 can be a passive vertical flow wafer formed of multiple layers of paper, or other porous material, designed to allow fluid to flow from one layer to another in multiple defined channels, and including dissolving reagent disposed at each layer to be used in desired biochemistry reactions. A final or outermost layer may be transparent to allow a camera or other light detection equipment to measure the intensity of light produced by bio or chemiluminescent reactions, or colour absorbance or reflectance for colorimetric reactions at the channel endpoints, or readout zones.

In some embodiments, receiving structure 140 can be a passive lateral flow wafer formed from a transparent material such as Polydimethylsiloxane (PDMS), and designed so liquid flows along channels in the PDMS picking up reagents at particular zones along the channels with the final zone being a readout zone as described herein.

In some embodiments, receiving structure 140 can include a hybrid of vertical and lateral flow channels and zones.

In some embodiments, receiving structure 140 can be formed from a transparent wafer material such as PDMS with electrical contacts on the front, side, or back that can be configured to power microfluidic valves and pumps to enable dynamic pumping of fluid through various channels and zones in order to take up reagents and produce the desired detection reactions. Such electrical contacts can be designed to contact with corresponding contacts fabricated on separation device 100 and to further contact an integrated corresponding electrode in a computing device such as computing device 1102, or a base station such as base station 134. A suitable controller under programming of the computing may be used to control, by way of the electrodes and electrical contacts, any microfluidic pumps and valves on receiving structure 140 or separation device 100.

In some embodiments, receiving structure 140 can be a Digital Microfluidic wafer (DMF) with electrodes physically contacting corresponding contacts in separation device 100 in contact with a computing device such as computing device 1102 or a base station such as base station 134, allowing suitable electrical voltages to be programmatically applied to various spots or zones in the DMF to control the fluid using a technique such as Closed Electro Wetting On Dielectric (EWOD).

In one embodiment, the sample receiving structure 140 comprises a plurality of layers of substrate (described further below) positioned over the outlet 118, such that upon alignment of the inner container aperture 110 with the outer container aperture 114, separated component(s) of the sample in the inner container 104 pass through outlet 118 and these layers.

In some embodiments, the reaction module 120 is designed so that any liquid exiting the aligned slots will encounter the "back" of the reaction module 120 and the sample passes through the layers of the sample receiving structure 140 until it reaches a final readout layer on an exterior of the device.

The aperture 114 of outer container 112 through to a face of the sample receiving structure 140 can be filled with a hydrophilic material, suitably pure cellulose, to act as a hydrophilic conduit and assist in the capillary flow of any fluid and minimize any void volume. In some embodiments, a hydrophilic conduit may be provided by other mechanisms, including other material.

As used herein, "reaction zone" refers to an area of substrate having deposited thereon or therein a reagent system specific for an analyte of interest which upon interaction with the analyte either produces a signal indicative of an assay value of an analyte of interest or produces a reaction product that upon being transported to a further reaction zone or zones produces a signal indicative of an assay value of an analyte of interest.

Suitably, the reagent systems are deposited onto the substrate and lyophilized. The reagent systems may suitable be deposited in association with a carrier, diluent or deposition aid. In one embodiment, the reagent system is deposited in association with gelatin or PVA. In one embodiment, PVA.

Figure 26:
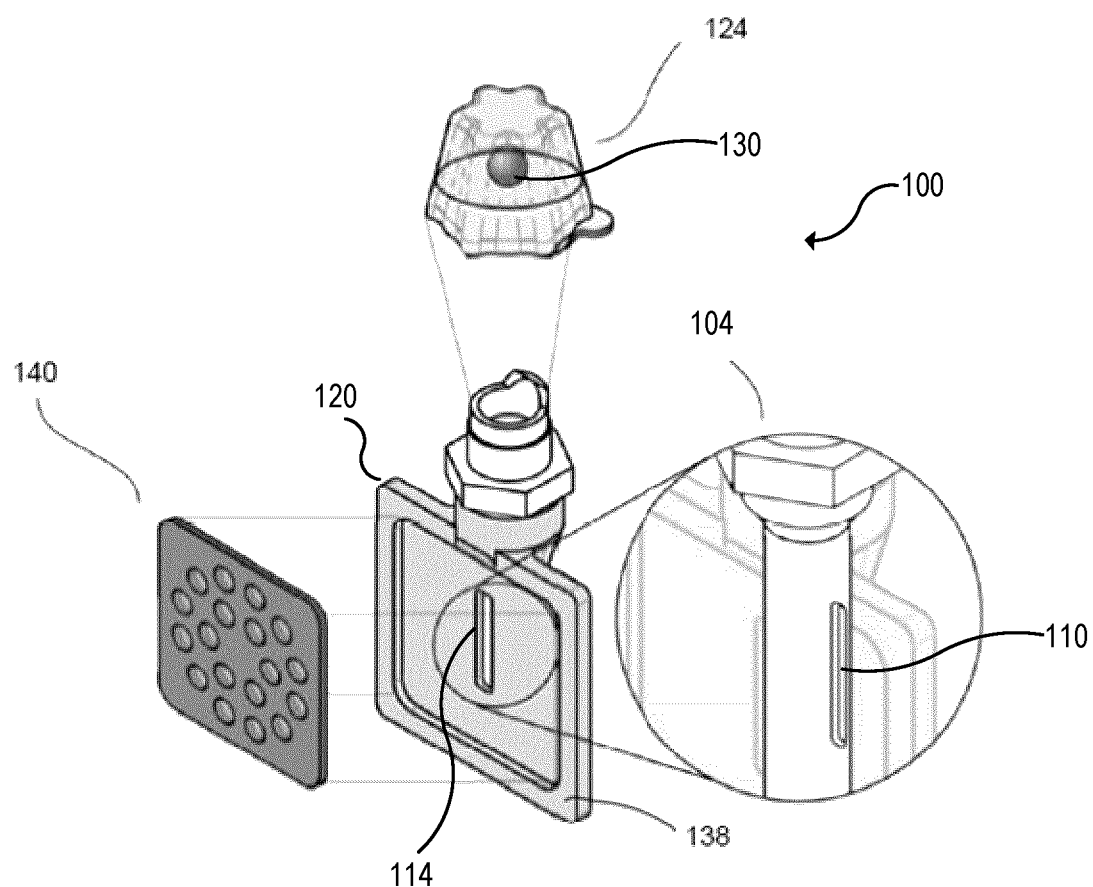
FIG. 26 is a schematic view of a fluid separation and analysis device according to an embodiment.

FIG. 25 shows a sample receiving structure 140 of a reaction module 120 according to one embodiment. FIG. 26 is a schematic view of device 100, including a sample receiving structure 140, according to an embodiment. In some embodiments, the device 100 is designed to hold a reaction module 120 in which multiple tests can be performed (i.e. the reaction module 120 include multiple channels). The reaction module 120 suitably uses technology such as vertical flow, laminated layers, and capillary flow microfluidics. Methods suitable for use in constructing the layers of the reaction module 120 can be found in *Three-dimensional microfluidic devices fabricated in layered paper and tape* Andres W. Martinez, Scott T. Phillips, and George M. Whitesides PNAS Dec. 16, 2008. 105 (50) 19606-19611; https://doi.org/10.1073/pnas.0810903105 (incorporated by reference in its entirety). In some embodiments, the reaction module sample receiving structure 140 includes one or more spreading layers (shown in FIG. 25 as a single spreading layer 142), one or more reagent layers (shown in FIG. 25 as two reagent layers 146a and 146b), and a readout layer 148. The sample receiving structure 140 may further include one or more filtering layers (shown in FIG. 25 as a single filter layer 144).

In some embodiments, the reaction module 120 uses a vertical flow technique whereby layers or sheets (reagent layers) with patterned hydrophilic/hydrophobic areas are laminated together, for example, one on top of each other in such a way as to provide channels 150a, 150b, 150c through which fluid will flow from one sheet to the next. In each sheet, zones for each channel may contain lyophilized chemicals which will dissolve and react with and/or in the fluid flowing through the zone during use. In some embodiments, channels and reaction zones can be otherwise patterned and otherwise provide structure through which a sample can be navigated.

In some embodiments, the pattern of hydrophilic zones surrounded by hydrophobic areas are created using photolithography ultraviolet light curing techniques and SU-8 negative photoresist. For example, the patterns are printed on cellulose acetate transparency sheets, transferred to SU-8 treated Whatman™ 1 paper and activated with a UV lamp. In some embodiments, an array of small hydrophilic circles surrounded by hydrophobic SU-8 is used for each reagent layer.

Various layers of a reaction module 120 according to some embodiments will now be described. In one embodiment, the first layer is a "spreading layer" 142, which is a thin hydrophilic layer. The spreading layer may be made from paper such as Technicloth from Texwipe or Porex Corporation filter material. The purpose of this layer is to quickly and evenly spread sample, which in one embodiment is diluted, partially sedimented plasma from the device 100 once the sample reaches this layer.

In some embodiments, the spreading layer 142 is directly affixed to a filter layer 144 via an adhesive layer 160a. This filter layer 144, may be affixed to the spreading layer 142 using, for example, patterned double-sided tape, such as ARcare® 90445Q from Adhesives Research Inc. whereby apertures are cut in the tape, the apertures forming part of the channels described above. These apertures are of the same size and aligned with the reaction zones. In some embodiments, the small space (gap between layers) caused by the thickness of the double-sided tape is filled with cellulose powder, as otherwise air in these spaces may impede flow from one layer to the next. Other means of affixing the layers will be known to those of skill in the art.

Other ways of adhering the layers of sample receiving structure 140 include a porous glue which adheres the layers while allowing fluid to flow thru, an example being polyvinyl alcohol, and pressure sealing the layers by way of an external structure that aligns and holds the layers in uniform contact with each other.

Examples of filter membranes include Pall Corporation's Vivid™ plasma separation membrane and Advantec's Mixed Cellulose Ester 3 um filter membrane.

In some embodiments, the filter layer 144 is followed by one or more reagent layers 146 laminated together. In one embodiment, the reagent layers 146 are connected using double-sided tape. In some embodiments, the final layer, the readout layer 148, is a rigid transparent layer made from material such as polycarbonate, acrylic, or polyethylene terephthalate, and can be affixed by tape. In any event, regardless of material used, the readout layer 148 should be completely or substantially transparent to permit analysis thereof.

Luminescent reagents, suitably in combination with PVA, are lyophilized into depression apertures formed by patterned tape. In some embodiments, luminescent reagents are lyophilized with a polysaccharide. Different shapes, number and arrangement of the apertures in the tape (which correspond to the reaction zones) are possible. The maximum number of apertures will be limited by the size of the reaction module 120, while the minimum number will be dictated by the number of tests to be performed, as will be further discussed below. While in one embodiment the number of reaction zones is not particularly restricted, a suitable number in view of the above considerations is between 3 and 30, preferably between 12 and 21. In one embodiment, the reaction module 120 has 18 reaction zones as shown in FIG. 8. As will be explained further below, in one embodiment, three reaction zones are provided for each analyte test.

In these embodiments, the separation device 100 is configured to provide three reaction channels for each test:

| Reaction Channel | Deposited System |
|---|---|
| 1 | reagent system specific for an analyte of interest, which will be solubilized by the sample/analyte containing fluid and react with the analyte |
| 2 | reagent system and known amount of analyte of interest designated Calibrator 1 |
| 3 | reagent system designated Calibrator 2 with a known amount of analyte of interest slightly higher than Channel 2 such that both are within the appropriate reference ranges for such a test analyte and can be used to determine the analyte concentration using the method of standard addition |

While for convenience, the reaction channels above are identified as channels 1 through 3, it should be understood that sample may reach final reaction zones in each channel concurrently or near concurrently and are analyzed concurrently. Reaction channels 2 and 3 are provided as calibrator. These channels have deposited thereon or therein known quantities of analyte to be tested. In one embodiment, channel 1 may have no analyte deposited therein, while in another embodiment, all three channels may have deposited therein known amounts of analyte. By applying the Method of Standard Addition, the concentration of the analyte can be determined. Further details regarding the method of standard addition can be found in Harris, Daniel C. (2003). *Quantitative Chemical Analysis* 6th Edition. New York: W.H. Freeman and A systematic approach to standard addition methods in instrumental analysis. Journal of Chemical Education. 57:703. Bibcode:1980JChEd . . . 57 . . . 703B. doi: 10.1021/ed057p703, both of which are incorporated by reference in their entirety. This can provide real time calibration and limit or eliminate system issues that might change over time causing errors, such as contamination of camera lens(es) and/or effects due to room temperature, humidity, etc.

In one embodiment, the reaction module 120 is manufactured separately from separation device 100 and is then connected to separation device 100. In one embodiment, reaction module 120 is sized to fit in a recess of the separation device 100, where it may be secured in place such as by gluing in place along the edges using UV activated glue.

Suitably, a small air vent 162 is made through the readout layer, shown in FIG. 8 as positioned near the top on each side. The air vent 162 helps to draw the separated fluid to reaction zones 152a, 152b, 152c.

In some embodiments, reagents are deposited into the reaction zones 152a, 152b, 152c, on the reagent layers by spotting exact volumes of the desired mixed reagents, optionally in a gelling medium such as 0.2-2% PVA in PBS or similar concentrations of pectin or gelatin. After deposit, the zones are dried, for example, using lyophilization techniques. The present inventors have surprisingly found that this combination of PVA in PBS or similar concentrations of pectin or gelatin provides an effective medium for depositing the reagents, which can be readily lyophilized. Accordingly, in one embodiment there is provided a method of immobilizing reagent(s) on a reaction surface comprising combining the reagent(s) with 0.2-2% PVA in PBS, pectin and/or gelatin, depositing this combination onto the reaction surface and lyophilizing the deposited combination.

Method of Separation of Blood

Also provided is a novel method of separating plasma from whole blood. Specifically, there is provided a method for sedimentation of blood and using polyvinyl alcohol (PVA). This can be used to facilitate and/or enable measurements or testing of one or more analytes in blood plasma, for example. While in some embodiments, this method of sedimentation may be used in association with device 100, in other embodiments, this novel method may be applied independent of any specific device and, accordingly, in one embodiment, the context in which this method is used is not specifically restricted.

This method for separating components in blood via sedimentation is particularly suited for microfluidic plasma separation.

While it is known that gelatin, PVA and other additives may increase the sedimentation rate of blood [*The use of Pectin and Gelatin in the Processing of Plasma* in the Blood Bank Milton Gjelhaug Levine, M.S., PhD. Robert E. Hoyt, M.S., PhD.]. The present inventors have surprisingly found that PVA of a specific molecular weight range may be used in small quantities for the efficient sedimentation of plasma from whole blood and, in particular, for the efficient separation of microfluidic quantities of plasma from whole blood.

Accordingly, in one embodiment, there is provided a method of sedimenting whole blood for the purpose of plasma separation. The sample or portion thereof is sedimented using PVA. For example, the sample is diluted by two parts diluent to one part blood where the diluent is 0.2% to 0.9% weight/volume concentration of PVA having a molecular weight of 50,000-250,000 Daltons, in one embodiment, 50,000 to 205,000 Daltons, in one embodiment 205,000 Dalton PVA 70-100% hydrolyzed, in one embodiment 88% hydrolyzed (e.g., Mowiol 40-88 from Sigma) suitably in PBS buffer This method is suitable for sedimenting small volumes of whole blood and, in particular, volumes less than 5 ml, including volumes less than 1 ml, and less than 0.5 ml. The use of PVA as described above enables complete or substantially complete sedimentation of cellular material from whole blood in a matter of minutes, and in the case of sample volumes described here, less than 5 minutes.

Dilution, mixing, and/or sedimentation may be facilitated by physical displacement, for example, by inversion or movement of a sample container. This can be further facilitated by a mixing structure (e.g., mixing ball bearing) contained within the container. The mixing structure is suitably denser than the components to be mixed without taking up much volume.

In one embodiment, the sedimented sample or portion thereof is separated to remove the plasma component, from the remaining blood components and may optionally be further filtered. In one embodiment, these subsequent steps are performed using device 100.

The filtered components (e.g., filtrate) can be used in analyses, for example, that detect a quantity of one or more components. These analyses may involve chemi- or bioluminescence reactions, for example. Other examples can include spectroscopy, spectrometry, photometric, fluorescence, or other analytical quantification techniques. In this way, one or more components in a sample of blood can be detected and/or measured.

Calculating Dilution Factor

Calculation of a dilution factor will now be described in relation to a sample that is blood. In some embodiments, where initial whole blood is prediluted, it is necessary to know the dilution factor to properly calculate any analyte concentration in the plasma. Further, because it may be difficult to measure volumes of small amounts of blood in systems such as those described herein that may be operated by the end-user rather than a technically skilled person, the amount of whole blood collected will not be precisely known. Also, since the hematocrit of each person can be significantly different, the amount of plasma in the sample is not readily known.

In some embodiments, this problem is addressed by adding a known concentration of a soluble chemical/analyte, not normally in or reactive to blood, into the diluent and then testing for this analyte using the testing protocol described herein. Knowing the final and initial concentration of this analyte, the dilution factor can be calculated and it will be true for all analytes in the blood. Examples of analytes for performing the dilution factor test are presented below. The dilution factor of plasma (DFp) can be calculated as DFp=VT/VP where VT is sum total of the volume of the plasma (VP) plus the volume of the diluent (VD). When performing a test on diluted plasma, after analysis and measuring the concentration of an analyte, [Xr] in the dilution, the result is multiplied by the DFp to determine the true analyte concentration, [X] in the actual patient plasma. ([X]=DFp*[Xr]). A corollary is DFp=[X]/[Xr]. Similarly for the dilution factor of the diluent, DFd=VT/VD and Dfd= [Y]/[Yr] where [Y] is the actual concentration of an analyte in the diluent and [Yr] is the measured concentration. It can be readily shown that there is a relationship between DFp and DFd, that being DFp=DFd/(Dfd−1) and DFp=[Y]/([Y]− [Yr]). So by measuring the diluted concentration of an analyte in the diluent, and knowing the initial concentration, the dilution factor of the plasma can be calculated without actually knowing the volume of blood or plasma collected. These calculations can be performed using a processor and the processor can receive one or more measurements as input and/or facilitate or obtain the measurements.

In some test methodologies, such as with CB, the volume of plasma used in a reaction, diluted or otherwise, may be critical in comparison with the calibrators. It may be desirable to have known volumes or volumes known to be the same as calibrator(s). Note, it may be the fluid volume that is important, rather than the volume of the space that is designed to hold the fluid as the fluid volume might be less for whatever reason. Without knowing volumes, the concentration of a measured analyte (amount per volume) may not be calculated. As well, most CB readout reactions are rate-based (how much light is generated over a delta time) [see e.g. *Tietz Fundamentals of Clinical Chemistry*, 6th Edition, Carl Burtis David Bruns, incorporated by reference in its entirety]. Due to the small amounts of plasma and variances in microfluidic channels widths, minor obstructions in or lengths of fluid paths and layer thickness, reactions in the sample and calibrator channels might not happen simultaneously nor with the same fluid volumes.

Accordingly, adding a known concentration of a soluble chemical/analyte, not normally in or reactive to blood, into the diluent and then providing a reaction zone with a reagent system to test for this analyte can address this problem.

Method of Separating and Analyzing Blood Plasma Using Device 100

An example method for separation of biological components is described in relation to a separation device 100 (including a reaction module 120) used to separate components in blood (e.g., via sedimentation for microfluidic plasma separation), according to some embodiments.

With reference to FIGS. 27A, 27B, 27C, 27D and 27E the method includes sample collection (27A), dilution (27B), mixing (27C), sedimentation (27D) and sample separation (27E). Following separation, the blood plasma is analyzed at reaction module 120.

As will be described further below with reference to FIGS. 31 to 35, in some embodiments, analysis steps may be performed using a computer, for example, a computing device 1102 (such as a smartphone) of an imaging system 1100. Computing device 1102 may provide direction to a user on the timing and performance or one or more of the steps described below. Further, computing device 1102 may detect and provide an error message or signal when a step is performed incorrectly.

Figure 27A:
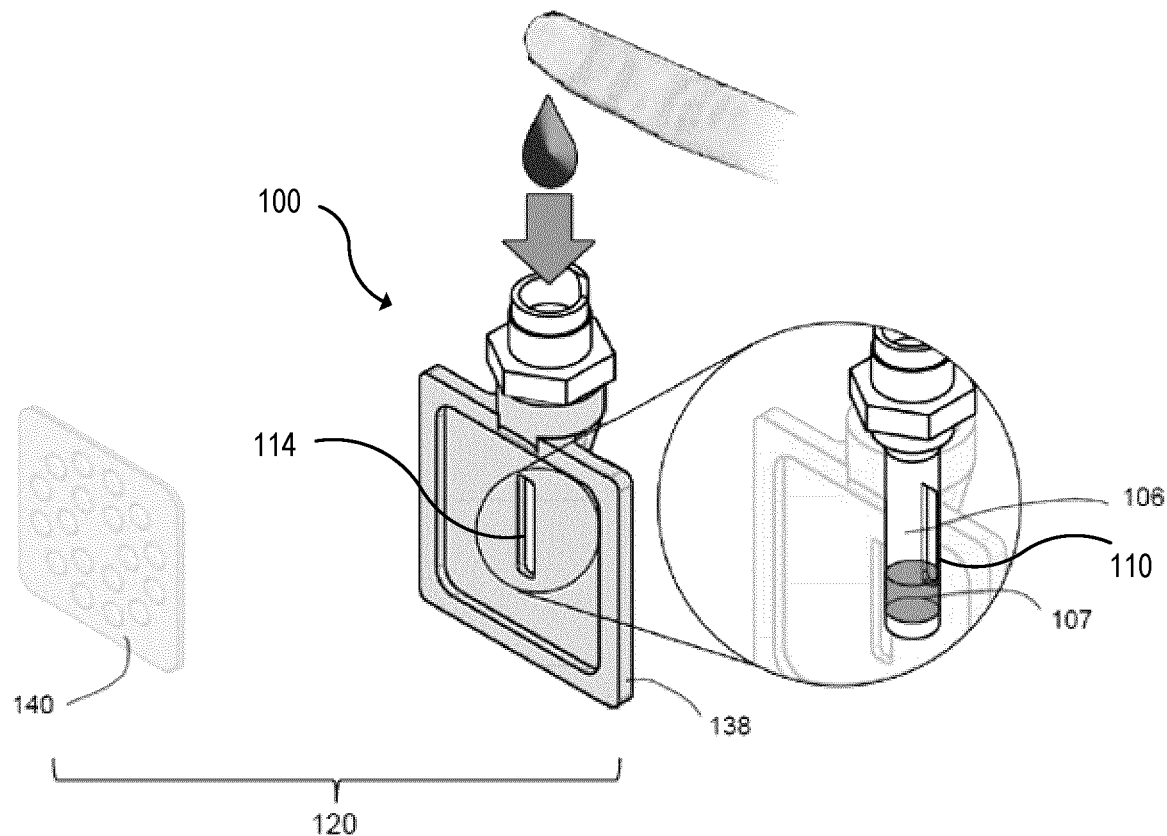
FIGS. 27A, 27B, 27C, 27D and 27E are schematic views showing sample collection (27A), dilution (27B), mixing (27C), sedimentation (27D) and sample separation (27E) according to an embodiment.
Figure 27B:
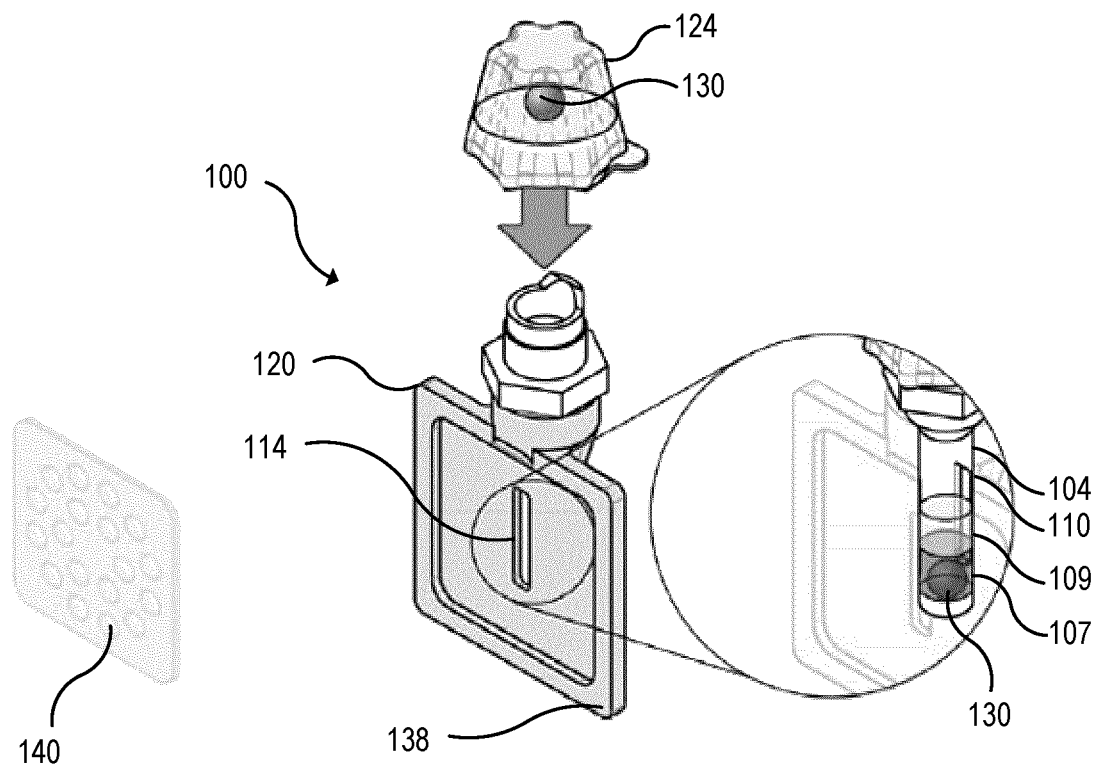

As shown in FIG. 27A, a user removes cap 124, removes cap spacer 126 and obtains a sample 107, suitably using sample obtaining structure 122. Separation device 100 typically collects about 1-3 drops of capillary blood from a finger prick, although the precise amount does not need to be known. As shown in FIG. 27B, the user then replaces the cap 124, the act of which breaches the diluent reservoir 116 diluting the sample with one or more diluents 109.

Figure 27C:
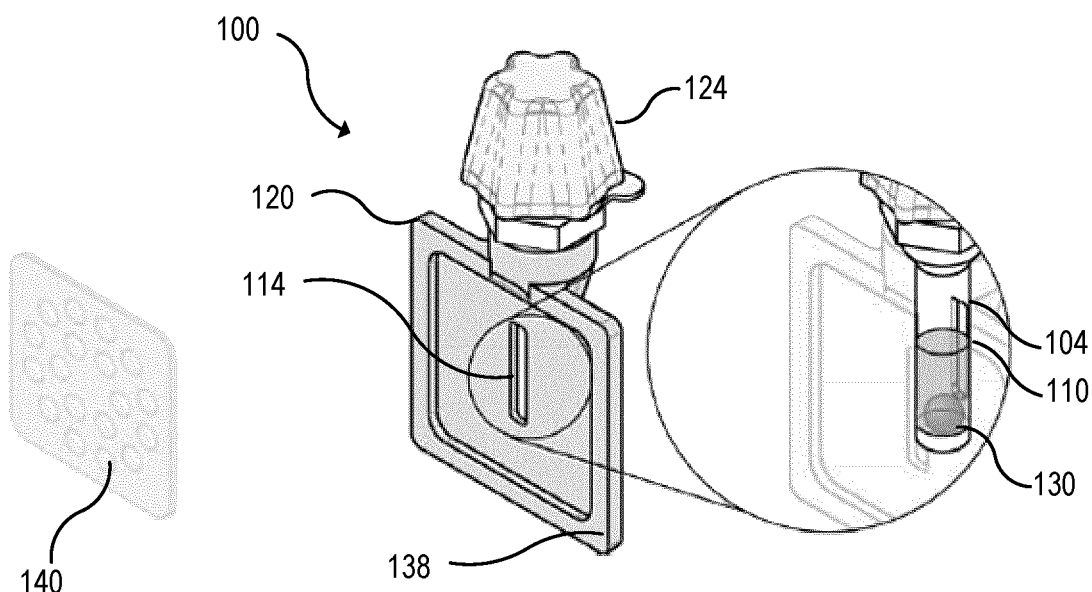

As shown in FIG. 27C the user suitably mixes the sample and diluent thereby promoting sedimentation by gentle rocking, inversion or agitation. This process will typically facilitated by a mixing aid such as ball bearing 130.

Figure 27D:
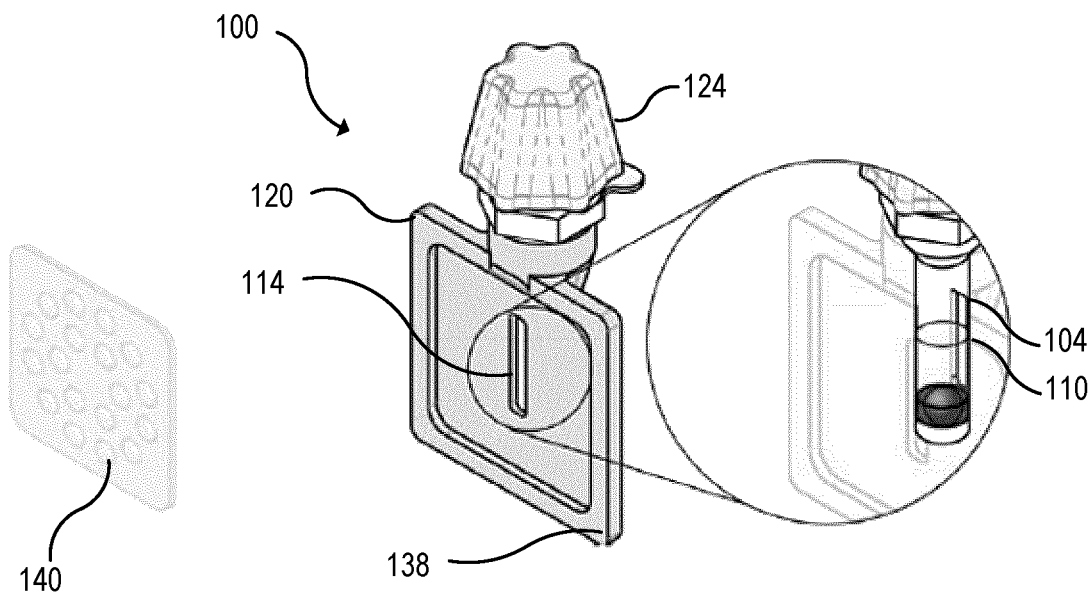

The separation device 100 partially sediments the whole blood, as shown in FIG. 27D. The sedimentation may occur quickly, for example, within one to five minutes, using a chemical additive in the diluent that greatly speeds up the sedimentation rate but which does not affect the blood for one or more or most plasma tests, and packs the cellular matter at the bottom of the container. A preferred embodiment is a ratio of 2 parts diluent to 1 part blood where the diluent is 0.2% to 0.9% weight/volume concentration of 50,000-350,000 Dalton PVA, preferably 205,000 Dalton PVA with 88% hydrolyzed (e.g., Mowiol 40-88 from Sigma) in PBS buffer. Separation device 100 can suitably be placed in base station 134 during sedimentation.

Figure 27E:
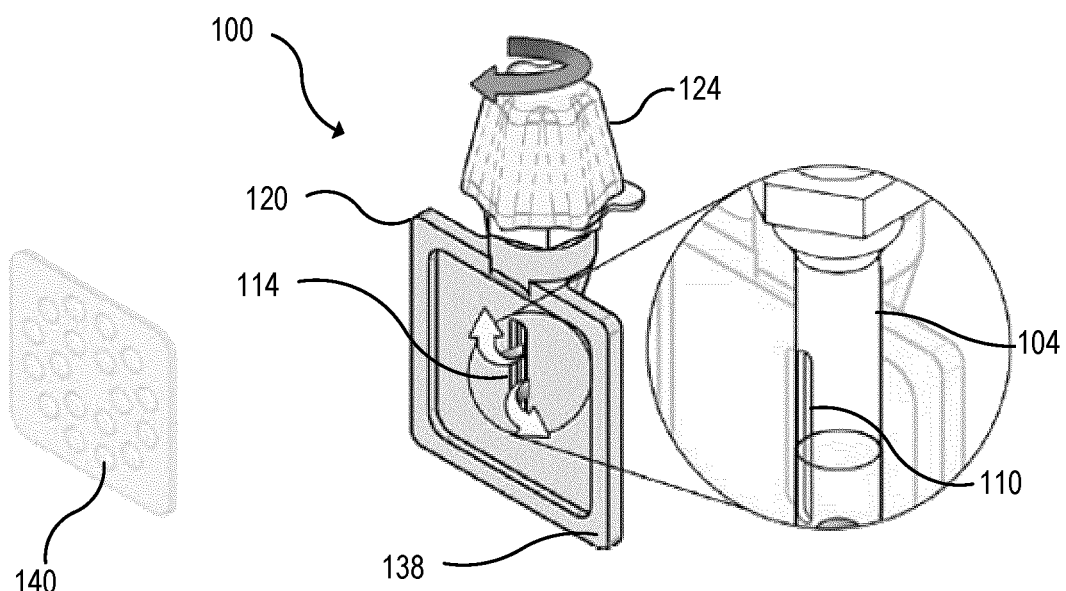

After a suitable sedimentation period has elapsed, the user removes the alignment tab 128, which permits the cap to be further screwed down, in one embodiment, the cap 124 can be turned clockwise by 180 degrees, aligning first aperture 110 and second aperture 114, whereby the dilute plasma passes through outlet 118 to reaction module 120, as shown in FIG. 27E.

As described above, the diluted plasma may be further filtered in the reaction module 120 to remove any remaining cellular matter not removed through the sedimentation and separation process described above. The diluted plasma moves through the reaction zone(s) described above until it reaches the readout layer 148, where it is subject to analysis, typically using a computing device 1102 such as a smartphone, as described further below with reference to FIGS. 31 to 35.

The results of the analysis may be presented to the user or communicated to another party e.g. a medical professional.

In this way, a point of care device can be provided that allows an unskilled user to conduct and/or receive one or more test results based on a small sample of blood. This may be quickly accomplished without the need for a physician or laboratory technician or transport of sample to different facilities.

In some embodiments, one or more of the measurements or calculations are conducted using a smartphone camera, integral computer processor, and an application tailored, compatible with, and/or developed for the separation device 100. In some embodiments, the plasma is completely filtered before providing the plasma to the reaction channels. In some embodiments, the reaction channels are embodied in one or more of a variety of configurations and/or geometries and one or more different combinations of channels can be used together, for example, to facilitate appropriate reaction measurements and/or analyte concentration calculations. The reaction module and layers may be as described in more detail herein.

In some embodiments, separation device 100 is designed or configured to allow for shelf storage depending on the specifications of the reagents used. For example, separation device 100 may be stored in a refrigerator at 4 or −20 degrees Celsius.

Figure 28:
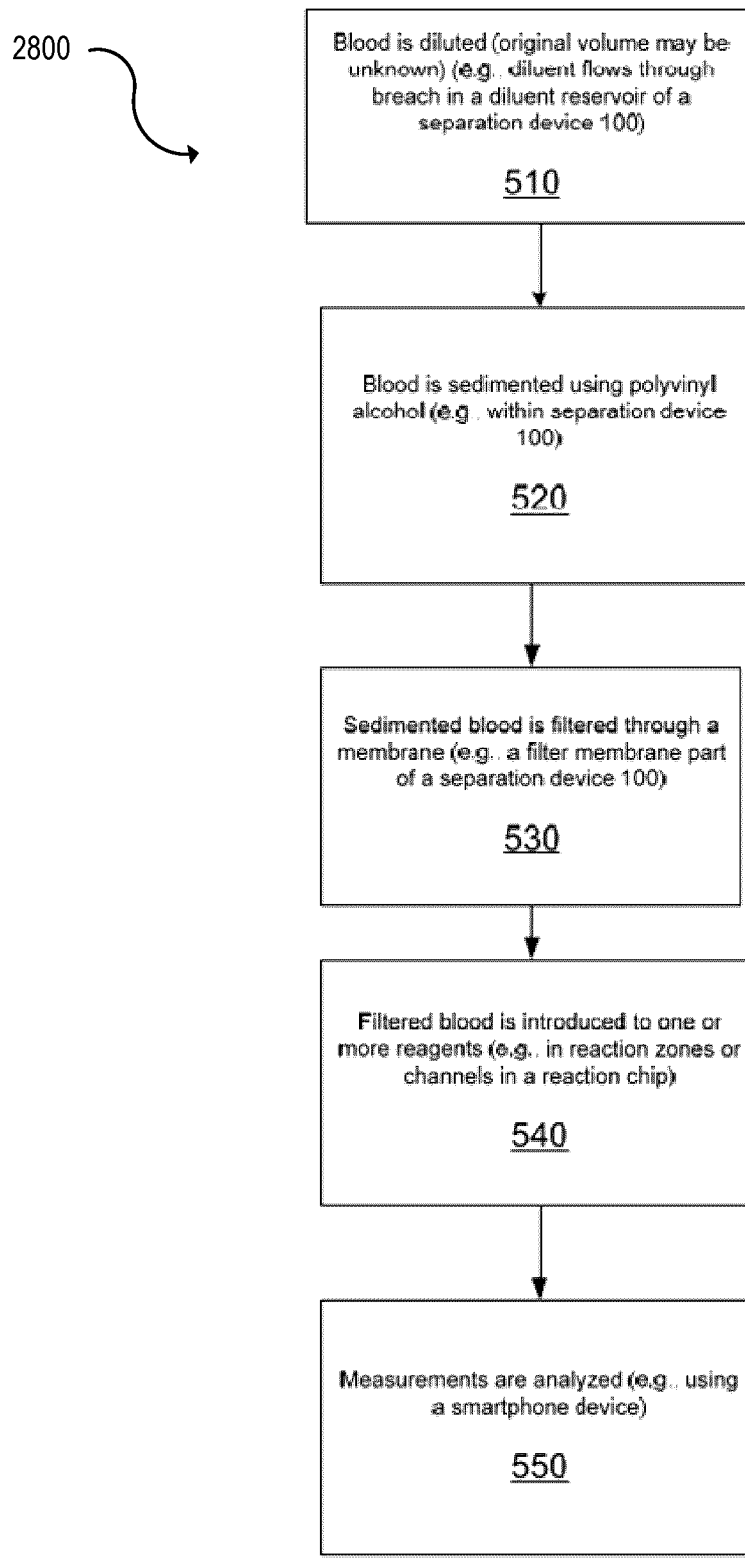
FIG. 28 is a flow diagram of an example method for separation of components, according to an embodiment.

FIG. 28 is a flow chart of an example fluid analysis process 2800 performed on blood, including some of the steps of the method of separation of biological components as shown in FIGS. 27A to 27E, including sample collection (27A), dilution (27B), mixing (27C), sedimentation (27D) and sample separation (27E).

Certain steps of fluid analysis process 2800 may be performed using components of separation device 100. As described further below with reference to FIGS. 31 to 35, in some embodiments, certain steps of fluid analysis process 2800 may be performed using a computer, for example, a computing device 1102 (such as a smartphone) of an imaging system 1100

As illustrated in FIG. 28, fluid analysis process 2800 may include steps 510 to 550, described in further detail below.

A fluid sample, for example, a blood sample, may be collected at separation device 100, as shown, for example, in FIG. 27A.

At step 510, the blood is diluted (original volume may be unknown). Diluent 109 may flow through a breach in a diluent reservoir 116 of separation device 100, as shown in FIG. 27B.

At step 520, blood is sedimented using polyvinyl alcohol (e.g., within sedimentation compartment 106 of separation device 100), as shown in FIGS. 27C, 27D.

After a suitable sedimentation period has elapsed, a user may actuate separation device 100 to pass the dilute plasma (sedimented blood) through outlet 118 to reaction module 120, as shown in FIG. 27E.

At step 530, sedimented blood is filtered through a membrane (e.g., a filter layer 144 of receiving structure 140).

At step 540, filtered blood is introduced to one or more reagents in receiving structure 140 (e.g., in reaction zones such as 152a, 152b, 152c or channels such as 150 (150a, 150b, 150c) in receiving structure 140).

At step 550, measurements may be taken of reactions occurring in a readout layer 148 of receiving structure 140, such as image data captured by an image sensor of a camera, and the measurements are analyzed, typically using a computing device 1102 such as a smartphone, as described further below with reference to FIGS. 31 to 35.

Point of Care Analysis

In some embodiments, separation device 100 is used in conjunction with a smartphone or other modern digital camera. Such cameras employ color filters to separate Red, Green, and Blue wavelengths, or bandwidths, of light into separate intensity measurements which are digitized and stored. So an image can be stored in the smart phone as a massive array of individual pixels with 3 measured intensities (RGB), for example. Using chemi and bioluminescence reactions, for example, and by choosing independent reaction methodologies that do not interfere with each other and produce light at wavelengths that would result in such light being recorded in separate channels by the camera, two tests (or three or more) tests can be conducted at the same time. An example of a volume test is described herein. Where the processor is configured to divide the light intensity measured for the sample analyte by the light intensity measured for the volume test, all channels can be normalized for volume. By taking repeated images from the camera it can be determined within a few seconds when the light-producing reactions start (e.g., when light above background is found) and therefore light producing reactions that follow a normal time decay curve and be adjusted for relative start time.

Various comparisons and/or normalizations can be conducted in relation to one or more threshold values for one or more different image-related characteristics. For example, in some embodiments, the processor is configured to actuate an analysis unit once detected light exceeds a threshold background light value. A computer-readable medium stores machine-interpretable instructions to configure a processor to configure an analysis unit that can receive data (e.g., light-related measurements and/or associated data, analyte-related measurements and/or associated data, chemical and/or bioluminescence measurements and/or associated data) and generate one or more test characteristics such as a concentration of analyte in an original blood sample.

In some embodiments, a CB reaction methodology may be implemented that may not interfere with any test methodologies to be employed on the separation device 100. This method may also produce light at a bandwidth picked up by a different color filter on the camera than that for the tests to be conducted on the separation device 100. For example the method might produce light picked up by the blue filter while the tests to be performed would be designed to only be picked up on the red filter.

An example method of analyte selection according to some embodiments is described as follows. By choosing an analyte normally found in a blood sample, for example, alkaline phosphatase, or by adding an analyte to a diluent provided to the sample, and by adding the same amount of appropriate reagents to each and every channel in the test device, including the calibrators so that these reagents, using a methodology described herein can produce light. This analyte and methodology can be designed to produce light at a rate and in a linear fashion based on the amount of analyte in the sample that has reached the readout zone. Based on the design in these embodiments, the concentration of analyte can be the same for all channels and zones as noted, although the volumes at any specific time may be different.

Other analytes that may be used in various embodiments to produce luminescent reactions include akalumine (reacts with ATP to produce light), firefly luciferase, NanoLuc™ Luciferase, HyperBlu and Aquaspark ALk both of which react directly with Hydrogen peroxide to produce characteristic blue and green light.

In some cases, where volumes and dried reagents are equal, readout zones (e.g., in a reaction module or other reaction device) would show the same light intensity for an analyte over the same time period. However, if the volumes are different this would directly and proportionally change the amount of A and thus the amount of light over a certain period of time (over the whole readout zone) may be different. A method (e.g., using separation device 100) described herein can be used to obtain one or more analyte measurements by taking an image (e.g., picture) with a chosen exposure time (or, in some embodiments, a number of pictures over a period of time) of all reaction zones at the same time and measuring or extracting data indicating the light intensity. The intensity measurements of light can be proportional to the sample volume at the readout zone.

In some embodiments, this same picture also captures or measures the actual analytes being tested but on different filter bandwidths of the camera. In some embodiments, the analyte chosen and the reagents used for this test are selected to not interfere with an actual analyte that is the subject of a test. Further, the two independent tests may be measured at the same time. Dividing the intensity of the test analyte by the intensity of analyte in the sample and calibrator readouts can normalize for volume and account for volume variance inaccuracies.

In some embodiments, on each separation device 100 is attached a near field communications (NFC) chip that can identify model number, lot number, tests, and/or other characteristics that are available on the device and any other information for the performance of successful tests. This information can be transmitted and/or received by the separation device 100.

Integration with Mobile Device in an Imaging System for Analysis

In some embodiments, the separation device 100 is designed to be implemented as part of an imaging system, including a smartphone, having a camera utilized as a readout or measurement device, and a processor of the smartphone to perform analysis of an image of separation device 100, for example, to determine the intensity of bandwidths for each pixel in the image of separation device 100 and instances of chemiluminescent and/or bioluminescent reactions in plasma that has been separated and diluted using techniques described herein.

Figure 31:
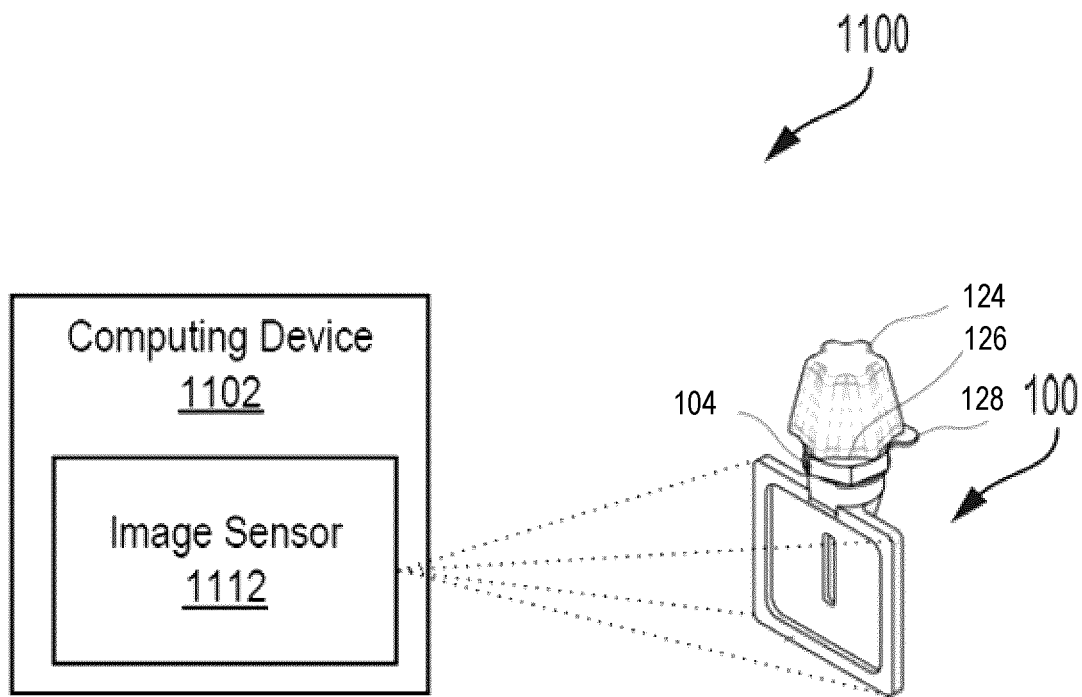
FIG. 31 is a simplified schematic diagram of an imaging system, according to an embodiment.

FIG. 31 depicts an imaging system 1100 suitable for obtaining and analyzing images, for example, of separation device 100, such as images of chemiluminescent and/or bioluminescent reactions. In some embodiments, imaging system 1100 includes a computing device 1102 having an image sensor 112. In use, image sensor 1112 captures image data, for example, an image of separation device 100. In an example, image data may represent an image of reaction zones 152c, 153c on readout layer 148 of receiving structure 140 of separation device 100, such as those shown in FIG. 25. Said image data is processed by computing device 1102, as described in further detail below. Imaging system 1100 may also include a base station 134.

In some embodiments, image sensor 1112 captures an image of a fluid sample, for example, a diluted biological fluid sample such as plasma that has been separated from whole blood, diluted, and reacted with reagents in separation device 100, as described herein. The image data may include image elements identifying instances of light intensity. Computing device 1102, upon receiving the image data, may correlate the image elements with instances of a reagent or luminescence reaction. For example, this may include photometric, chemiluminescence, bioluminescence, electro chemiluminescence, and fluorescence measurement methods to identify analytes and/or reactions, as described herein.

In some embodiments, a dilution factor of the fluid sample, such as plasma, represented in the image data may be determined by computing device 1102, as described herein. A relative volume of fluid between, for example, reaction zones of separation device 100, may also be determined by computing device 1102, as described herein. The presence and/or concentration of an analyte or reaction of interest may then be determined, based on one or more of the observed image elements, dilution factor and relative volume of the fluid, using techniques as described herein.

Figure 35:
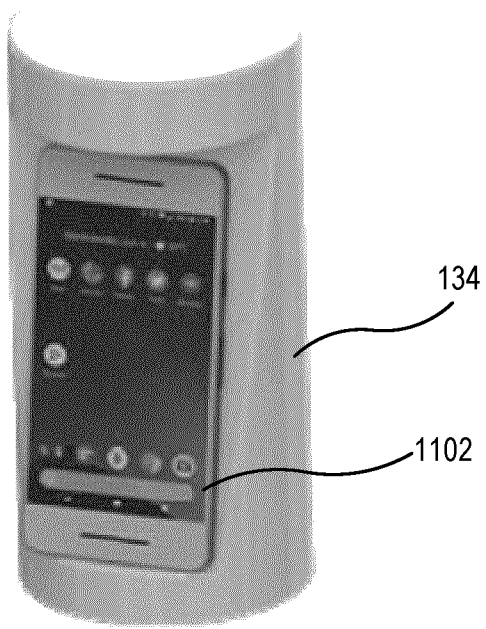
FIG. 35 is a front perspective view of a base station, according to an embodiment.

In some embodiments, computing device 1102 and separation device 100 may be used in conjunction with a base station 134, as shown in FIG. 35 and described in further detail below. Base station 134 may be used to align computing device 1102 and separation device 100, in use.

Components of imaging system 1100, including computing device 1102 and image sensor 1112, are described in further detail below.

Computing device 1102 can be any suitable electronic devices that interface with one another to provide complementary functions as described herein. Device 1102 may be a mobile computing device. For clarity in the discussion herein, mobile computing devices are commonly referred to as "mobile devices" or "devices" for brevity.

Example mobile devices include, without limitation, cellular phones, cellular smart-phones, wireless organizers, pagers, personal digital assistants, computers, laptops, handheld wireless communication devices, wirelessly enabled notebook computers, portable gaming devices, tablet computers, or any other portable electronic device with processing and communication capabilities. In at least some embodiments, mobile devices as referred to herein can also include, without limitation, peripheral devices such as displays, printers, touchscreens, projectors, digital watches, cameras, digital scanners and other types of auxiliary devices that may communicate with another computing device.

In one example, device 1102 may be a smartphone, or one may be a smartphone and the other a peripheral device (e.g., a speaker, a keyboard, a display screen, a camera). As will be apparent, other types of computing devices 1102 can be envisaged that have image capture and processing capabilities.

Image sensor 1112 can be any suitable image capture component, for example a camera including CMOS or CCD sensors. Image sensor 1112 may capture an image, such as an image of separation device 100, including, for example, images of chemiluminescent and/or bioluminescent reactions, such as those occurring in separation device 100.

Image sensor 1112 may be implemented with a camera lens (not shown) and optical filters (not shown) to separate intensities of red, green, and blue wavelength bandwidths of light coming in through the camera lens. In this way, computing device 1102 may digitize the intensity of bandwidths received for each pixel in an image.

Figure 29:
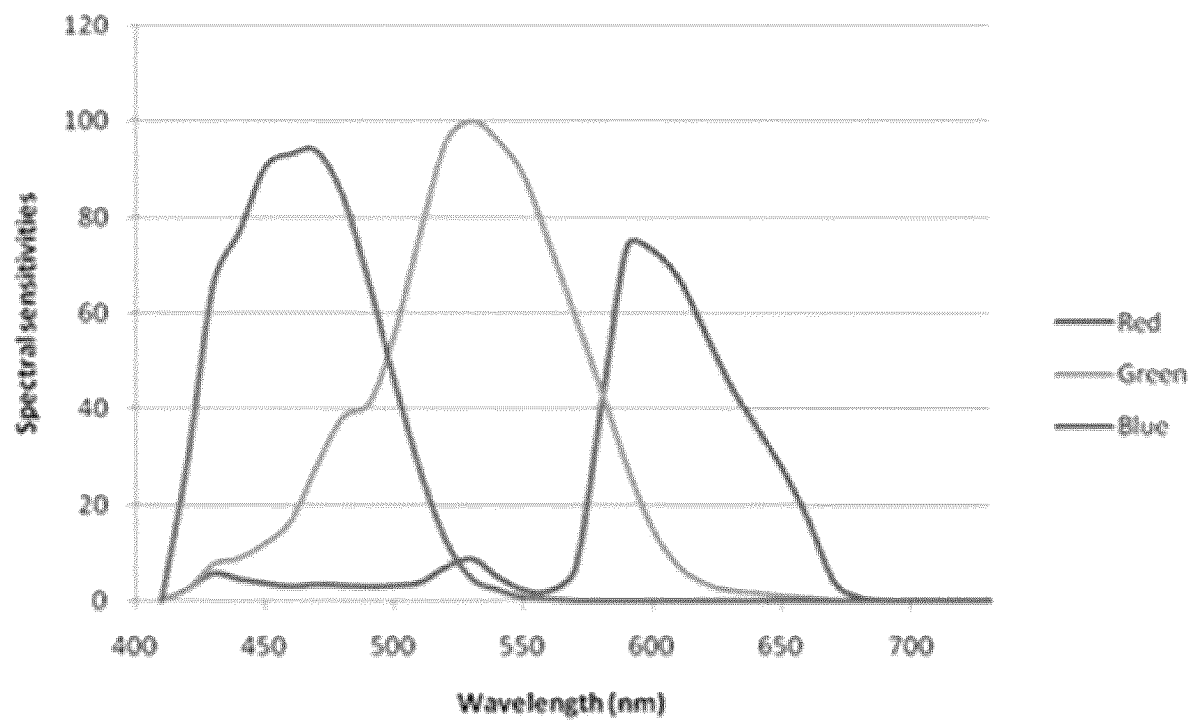
FIG. 29 shows a filter graph of a smartphone, according to an embodiment.

FIG. 29 shows the typical filter graph of a smartphone as an example. As shown, light with wavelengths of 410 to 550 will contribute to the relative intensity measured for blue but with wavelengths around 450 to 475 contributing more significantly to the blue. Wavelengths from about 400 to 625 also contribute to the intensity recorded for green.

In some embodiments, image sensor 1112 may be integrated with device 1102, or image sensor 1112 may be implemented as a separate hardware and/or software device.

As shown in an embodiment in FIG. 35, the base station 134 of imaging system 1100 may be an inexpensive device which can be designed for a specific computing device 1102 such as a smartphone, mobile device, or point of care device but can easily be redesigned for other such apparatuses. In some embodiments, the base station 134 has the following features and functionalities.

In some embodiments, the base station 134 is configured to sit flat on a table or desk, with a bottom surface to ensure it does not easily slip or tip.

In some embodiments, the base station 134 is configured with recess at 22.5 degrees (or a different angle) from vertical in which the designated computing device 1002 can be placed whereby the screen is readily accessible to a person sitting nearby. In the recess, there is a small circular transparent surface located where the device, e.g., smartphone camera lens, can be when seated. This recess is also designed to fit snugly with the device so that no light can penetrate through to the smartphone camera lens. The bottom and top as well as both sides of the recess will fit snugly around the device but can allow it to be easily removed.

In some embodiments, the base station 134 is configured to provide a similar transparent surface for an LED camera flash.

In some embodiments, the base station 134 is configured to have, internal to the base and adjacent to the transparent surface, a 10× macro lens enabling a 2.5 cm focal length for the seated camera. In some embodiments, the base station 134 can accommodate a different lens and focal length.

In some embodiments, the base station 134 is configured to have, at the top of the base, a slot or structure designed to allow seating of the separation device 100 at 22.5 degrees (or at another angle) from vertical and to a depth so that the center of the separation device's 100 reaction module is in 2.5 cm away and in direct alignment with the macro lens. The slot has a transparent surface, the exact size of the reaction module, so that there is a complete visual image of the reaction module from the smartphone camera, through the macro lens. This base station is designed so that no light penetrates into this internal area. In some embodiments, the sizes and configurations of any component of the base station can be altered to accommodate the different purposes described herein or inferred.

In some embodiments, the base station 134 is configured to have a top or cap 124 with the base station that, when placed on the base, will enclose the top of the seated separation device 100 so that no light can penetrate to the top of the reaction module. However, when the cap 124 is off, a person can readily place the separation device 100, turn the cap 124 of the separation device 100 clockwise 180 degrees, and remove the separation device 100 when finished.

In some embodiments, the base station 134 is configured such that when a camera is seated with the top on but no separation device 100 installed, computing device 1102 can capture and measure an image to ensure the transparent surface are not smudged or otherwise compromised to help ensure accurate measurements. Other such normalization or calibration functionalities can be provided in some embodiments.

During operation, computing device 1102 can also measure to make sure the separation device 100 is in place and proper alignment, to ensure no light is penetrating into the optical area before CB reactions take place.

In some embodiments, base station 134 may have one or more colour filters configured to be disposed between image sensor 1112 of computing device 1102 and separation device 100, which may allow for better isolation of different light wavelengths for identification as image elements in image data by computing device 1102.

In some embodiments, all or part of computing device 1102 may be integrally formed as part of base station 134.

Figure 32:
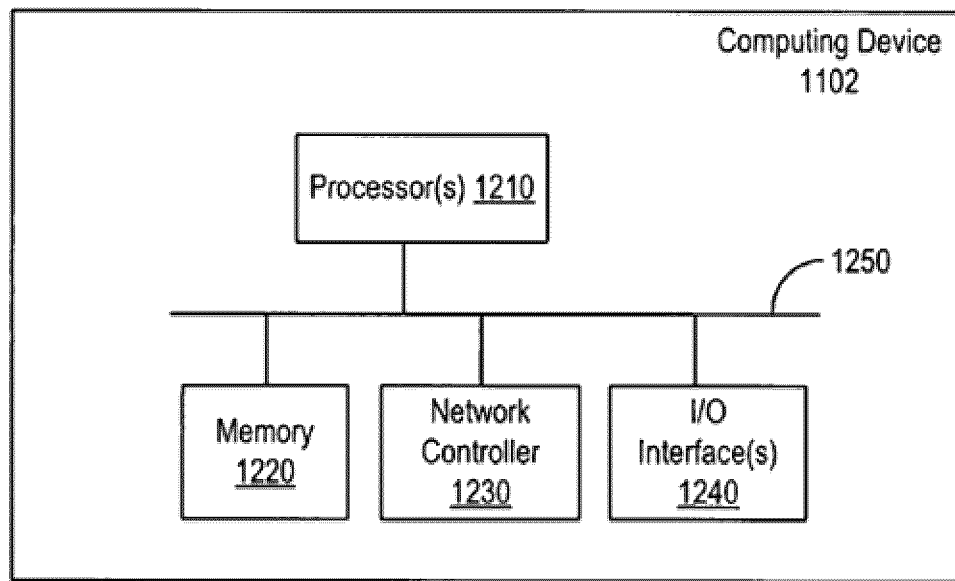
FIG. 32 is a block diagram of example hardware components of a computing device of the imaging system of FIG. 31, according to an embodiment.

FIG. 32 is a high-level block diagram of computing device 1102, for example, a mobile computing device. As will become apparent, computing device 1102, under software control, may receive image data for processing by one or more processors 1210 to analyze the image data. Processed image data, for example, detection of a luminescence reaction, may be displayed on device 1102 or communicated over a network to another device.

As illustrated, computing device 1102 includes one or more processor(s) 1210, memory 1220, a network controller 1230, and one or more I/O interfaces 1240 in communication over bus 1250.

Processor(s) 1210 may be one or more Intel x86, Intel x64, AMD x86-64, PowerPC, ARM processors or the like.

Memory 1220 may include random-access memory, read-only memory, or persistent storage such as a hard disk, a solid-state drive or the like. Read-only memory or persistent storage is a computer-readable medium. A computer-readable medium may be organized using a file system, controlled and administered by an operating system governing overall operation of the computing device.

Network controller 1230 serves as a communication device to interconnect the computing device with one or more computer networks such as, for example, a local area network (LAN) or the Internet.

One or more I/O interfaces 1240 may serve to interconnect the computing device with peripheral devices, such as for example, keyboards, mice, video displays, and the like. Such peripheral devices may include a display of device 1102. Optionally, network controller 1230 may be accessed via the one or more I/O interfaces.

Software instructions are executed by processor(s) 1210 from a computer-readable medium. For example, software may be loaded into random-access memory from persistent storage of memory 1220 or from one or more devices via I/O interfaces 1240 for execution by one or more processors 1210. As another example, software may be loaded and executed by one or more processors 1210 directly from read-only memory.

In some embodiments, computing device 1102 may be an embedded system or microcontroller, including a processor, memory, and input/output (I/O) peripherals on a single integrated circuit or chip, to perform the processes and store the instructions and data described herein. In an example, computing device 1102 may be a microcontroller such as an Arduino board and associated software system.

Figure 33:
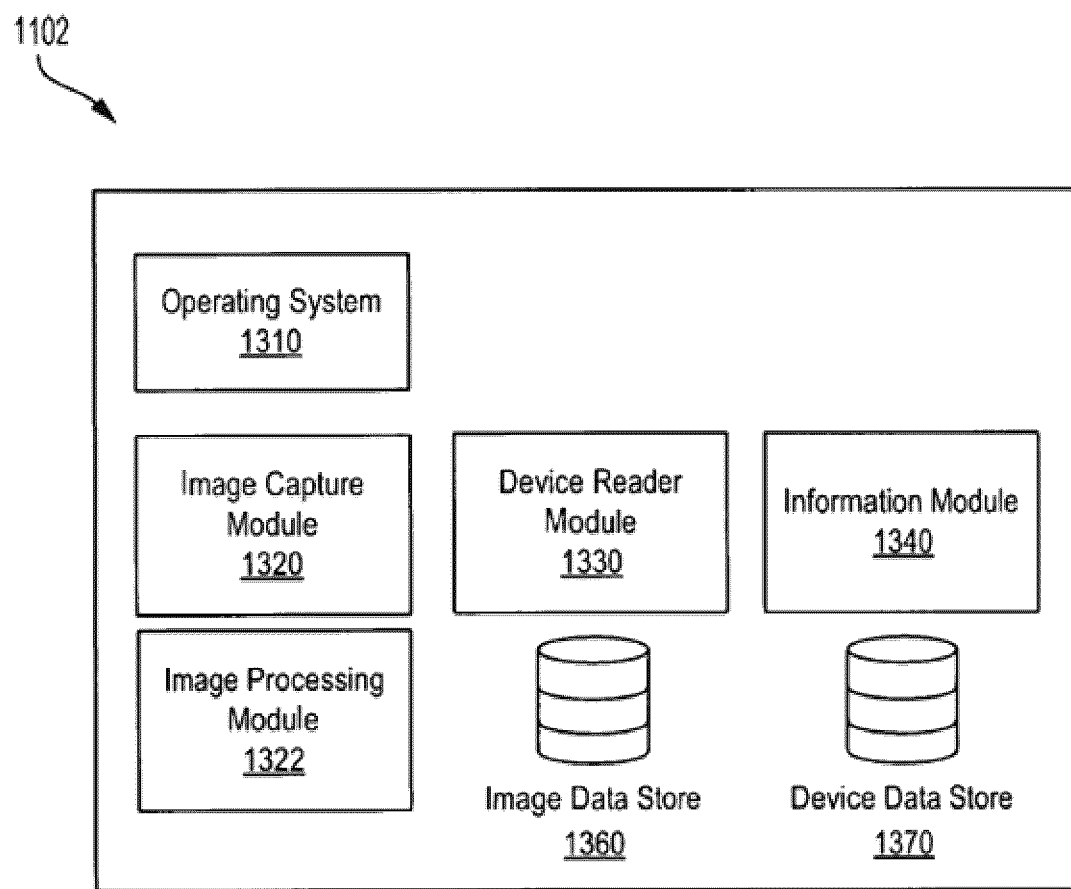
FIG. 33 illustrates the organization of software at the computing device of FIG. 32.

FIG. 33 depicts a simplified organization of example software components and data stored within memory 1220 of computing device 1102. As illustrated, these software components may include operating system (OS) software 1310, image capture module 1320, image processing module 1322, device reader module 1330, information module 1340, image data store 1360 and device data store 1370.

Operating system 1310 may allow basic communication and application operations related to the mobile device. Generally, operating system 1310 is responsible for determining the functions and features available at device 1102, such as keyboards, touch screen, synchronization with applications, email, text messaging and other communication features as will be envisaged by a person skilled in the art. In an embodiment, operating system 1310 may be Android™ operating system software, Linux operating system software, BSD derivative operating system software, iOS™ operating system software, or any other suitable operating system software. In embodiments in which an Android operating system platform is in use, software components described herein may be implemented using features of a framework API (Application Programming Interface) for the Android platform.

Image capture module 1320 operates in conjunction with image sensor 1112 and coordinates and controls operation of image sensor 1112, for example, by causing processor(s) 1210 to instruct image sensor 1112 to capture image data, for example, representing an image of a fluid sample in separation device 100, and in particular, chemiluminescent and bioluminescent reactions such as those in the fluid sample.

Image capture by image capture module 1320 may be prompted by instructions received from information module 1340, discussed in further detail below, relating to a state of separation device 100.

In some embodiments, image capture module 1320 may capture image data over a period or rate of time to represent the rate of light produced in a luminescent reaction over time. In an example, a series of image data may represent photons of light produced by a luminescent reaction, per second. The rate of luminescence may be correlated or directly proportional to a concentration of an analyte in a reaction.

Image capture module 1320 may also calibrate image sensor 1112 or measure calibration standards of image sensor 1112.

In some embodiments, image capture module 1320 may detect if image sensor 1112 needs to be cleaned or adjusted, based on the quality of image data produced by image sensor 1112.

Captured image data and calibration information may be stored in image data store 1360.

Image processing module 1322 analyzes image data of a fluid sample captured by image capture module 1320 and/or stored in image data store 1360. Image processing module 1322 may also utilize device data from device data store 1370, described in further detail below.

In some embodiments, image processing module 1322 is configured to identify instances of luminescence, such as chemiluminescent and/or bioluminescent reactions in the fluid sample, such as plasma that has been separated and diluted using separation device 100 and techniques described herein.

Chemiluminescent and bioluminescent reactions in a fluid sample in separation device 100 may be measured using image data captured by image sensor 1112, and by also measuring the calibration standards at the same time at different areas in the image data. As such, image data may contain image elements such as chemiluminescent and/or bioluminescent elements.

Image elements may be identified at a certain position within image data based on information received from device reader module 330 or information module 340. For example, device reader module 330 may identify where relevant reaction zones are positioned within separation device 100 for identification in the image data.

Similarly, a fiducial marker may be visible on separation device 100 to be captured in image data to provide a frame of reference for the image data such that the positions of various reactions may be identified, so as to identify image elements relating to luminescent reactions. Such a fiducial marker may allow for computing devices with different image sensors, or cameras, to be used, as different devices may align differently with separation device 100. A fiducial marker thus allows the image data to be calibrated to a field of reference, and is useful, for example, in identifying different reaction zones in which luminescent reactions may occur.

Figure 30:
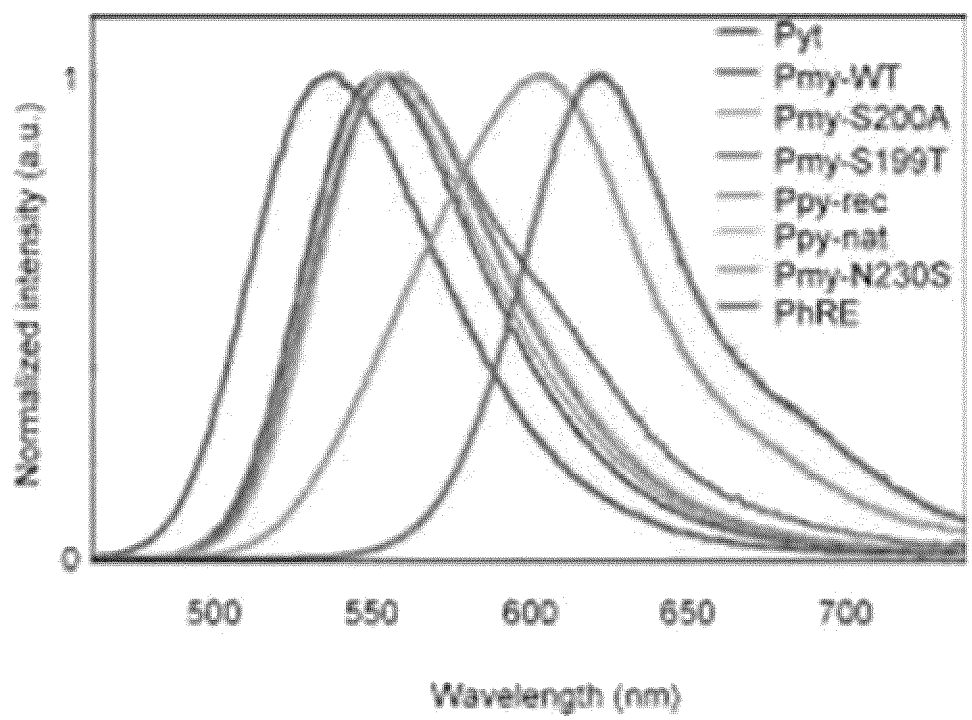
FIG. 30 shows selected chemi and bioluminescence reactions and their characteristic light bandwidth.

In chemiluminescence and bioluminescence, for example, there are many reactions, each with a characteristic light bandwidth. FIG. 30, for example, shows a number of bioluminescent reactions and chemicals. Processor(s) 1210 are thus configured to analyze image data, for example, by correlating image data to a characteristic light bandwidth, which may be used to predict or determine the presence of a reaction and/or chemical, for example an analyte concentration, in separation device 100.

For example, image data may be captured over a period of time, and certain image element colours, for example, associated with particular bandwidths, may be identified. The total number of instances of a particular colour or range of colour over time may be recorded and used to determine instances of a luminescent reaction, and in particular a volume or concentration of a particular analyte.

An image may be sampled a number of times to average out the light being generated over a period of time, which may improve the signal-to-noise ratio and display a decay curve of light produced in a luminescent reaction.

In some embodiments, multiple images may be captured by image capture module 1320 over the full time of one or more reactions. Image data associated with multiple images may be used to improve signal to noise ratios, as well as provide an ability to capture a light decay curve. Conveniently, this may improve accuracy of image analysis.

In some embodiments, image processing module 1322 may receive, for example, from an NFC tag on separation device 100 by way of device reader module 1330, information relating to the types of tests to be performed on a particular fluid sample in separation device 100, and the analytes that will be detected, as well as information relating to the location of reaction zones in separation device 100 where luminescent reactions may be expected.

Thus, image processing module 1322 may detect certain colour pixels, as image elements, at a known range or location in an image (correlating to a position of a reaction zone) to identify the image elements as corresponding to a luminescent reaction. The quantity of analytes performing such a luminescent reaction may then be extrapolated.

Using computing device 1102 at a point of care device to measure two (or more) independent reactions at the same time in the same zone may require careful selection of chemicals involved. In some embodiments, a method of blood sedimentation using PVA and/or a method of separation of blood or sample components described herein comprises this selection of chemicals.

Many chemical reactions using bio or chemiluminescent substrates can be similar and therefore interfere with each other if reacted together. They might also produce characteristic light in overlapping wavelengths that cannot be differentiated by the filters in a camera. However, reactions can be chosen that are both independent and produce light at discriminating bandwidths. For example, the chemical AquaSpark™ Broad Range Phosphatase Substrate available from Biosynth reacts in the presence of Alk Phosphatase (alkaline phosphatase) to produce a narrow bandwidth of light around 510 nanometers wavelength which can be picked up by both the blue and green filters. Bacterial luciferin, AkaLumine-HCl, available Sigma reacts with Adenosine triphosphate (ATP) in the presence of luciferase to produce a light bandwidth around 670 nanometers which will be picked up by the red filter but not the blue nor green. These reactions are independent and may not interfere with each other thereby allowing concurrent reactions in the same reaction zone, each designed to measure a specific but different analyte-one of which could be used for purposes of measuring relative volumes of each zone. One or more analytes can be measured from concurrent reactions in the same structure (e.g., reaction zone), in some embodiments. Examples of such chemistry are described herein.

Image processing module 1322 may be further configured to, based at least in part on the image elements identified in image data of a plasma, determine a dilution factor of plasma appearing in image data, as described herein, and a relative volume of plasma in separation device 100, as described herein.

Returning to FIG. 33, device reader module 1330 of computing device 1102 may receive information on separation device 100, for example, by way of near field communication ("NFC"). In some embodiments, device reader module 1330 may read NFC tag information on the separation device 100, to determine which tests are to be conducted and where to communicate results, for example, over the Internet.

An NFC tag on a separation device 100 may contain information related to where each reaction zone is located on separation device 100, and what is in each reaction zone (for e.g., which reagents and/or analytes are present in the reaction zone before a fluid sample is added to it, such as volume analytes and dilution analytes). Information from NFC may also indicate the types of tests being performed (for example, what test analyte is being detected). This information may be used by image processing module 1322 to identify various image elements in captured image data of a fluid sample, for example, in separation device 100.

Device reader module 1330 further maintains and/or updates device information relating to separation device 100, which is stored in device data store 1370.

In some embodiments, device 1102 communicates with separation device 100 using Bluetooth, NFC, or other types of wireless communications as envisaged by a person skilled in the art.

Information module 1340 is configured to cause processor(s) 1210 to display or present information or instructions to assist the user in the use and operation of separation device 100 and analysis of captured image data of separation device 100.

In some embodiments, information module 1340 may display or present information or instructions based on information received by NFC tag reader module 1330 relating to separation device 100.

For example, information module 1340 may provide a user, for example, by way of a display on computing device 1102, with timing and instructions on how and when to take a blood sample, put a cap on separation device 100, turn the cap so that the slits of the inner and outer cylinder line up, and place separation device 100 in base station 134. Information module 1340 may also receive inputs from the user, or for example detection of separation device 100 being placed in base station 134, indicating when certain steps are completed. As such, information module 1340 may indicate to image capture module 320 when to begin capturing images. In an example, once a user has disposed separation device 100 in base station 134, information module 1340 may receive notification. Image capture module 1320 may then be prompted to instruct image sensor 1112 to capture image data in intervals, for example, every ten seconds. Image capture module 1320 may retain only images once particular image elements are identified within image data.

Figure 34:
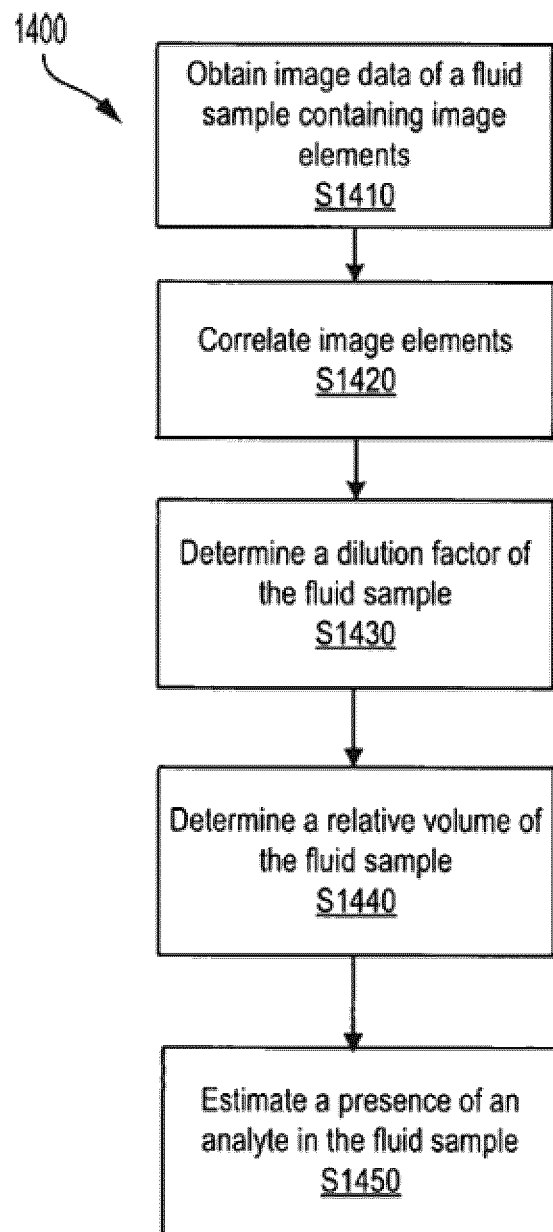
FIG. 34 is a flow chart of a method of processing an image of a separation device, performed by the software of FIG. 33, according an embodiment.

FIG. 34 illustrates a method 1400 of processing an image of separation device 100. Block S1410 is performed by processor(s) 1210 executing image capture module 1320. Blocks S1420 and onward are performed by processor(s) 1210 executing image processing module 1322.

At block S1410, image data is captured by image sensor 1112 representing a fluid sample such as plasma, for example at a readout layer of separation device 100, that has been separated from whole blood, diluted, and reacted with reagents in separation device 100, as described herein. The image data includes image elements identifying instances of light intensity.

In some embodiments, image data may be captured over a rate of time. For example, a rate of image elements, representing photons of light produced by a luminescent reaction, per second.

The rate of luminescence may be correlated or directly proportional to a concentration of an analyte in a luminescent reaction, as performed at block S1420.

At block S1420, processor(s) 1210 operate to correlate each of the image elements with instances of one or more reagent reactions to generate a correlation.

In an example, correlating includes comparing a measured relative intensity of the image elements, for example a colour, with characteristic light bandwidths of the one or more reagent reactions.

In some embodiments, correlation may be determined on the basis of the rate of image elements present in image data over time.

At block S1430, processor(s) 1210 operate to determine a dilution factor of the fluid sample. In some embodiments, determining a dilution factor includes estimating a final concentration of a first analyte or a dilution analyte in the fluid sample, based at least in part on the correlation, and comparing the final concentration of the dilution analyte with a known initial concentration of the dilution analyte that was added into the diluent.

In an example, calculating a dilution factor of the fluid sample may be performed using dilution factor test as described herein.

The dilution analyte may be an analyte that is not normally in nor reactive to blood, for example phosphoenolpyruvate (PEP) or sarcosine, as described herein.

At block S1440, processor(s) 1210 operate to determine a relative volume of the fluid sample in separation device 100, for example, as between reaction zones of separation device 100. In some embodiments, determining a relative volume of fluid sample in separation device 100 is based at least in part on identifying simultaneous and independent instances of a second analyte, or a volume analyte based, on the correlation.

In an example, three reaction zones of separation device 100 may each contain the same volume of a reagent, such as a phosphatase substrate. Two of the reaction zones are dosed with small but different amounts of the volume analyte, for example, dried and disposed in the respective reaction zones before use of separation device 100.

In testing a sample of plasma, the plasma, containing an unknown concentration of the volume/solvation analyte, is introduced to each of the three reaction zones.

The volume analyte may be, for example, alk phosphatase (alkaline phosphatase). The presence of volume analyte such as alk phosphatase may cause a regent such as a phosphatase substrate to react to produce a narrow bandwidth of light with a wavelength of around 510 nanometers. The volume analyte may be an analyte normally found in blood, or an analyte may be added to the diluent. A volume analyte may be selected, with a respective reagent, to produce different bandwidth(s) of light than that produced by other analytes, such as dilution analyte and test analyte, being measured.

By identifying the luminescence produced, techniques such as the method of standard addition, or other suitable techniques, can be utilized to determine the concentration of the volume analyte in the fluid sample and thus a relative volume of fluid sample in each reaction zone of separation device 100.

The luminescence produced by volume analyte may also indicate two parameters: (i) how well the dried volume analyte pre-dosed in each reaction zone dissolves in the plasma sample, and (ii) the amount of volume analyte present in the plasma sample, each producing a luminescent reaction. The luminescence may thus indicate a solvation normalization of the reaction solution.

At block S1450, processor(s) 1210 operate to estimate a presence or concentration of a third analyte, or a test analyte, in the fluid sample based at least in part on the correlation, the dilution factor and the relative volume.

The test analyte may be, for example creatinine. In some embodiments, the test analyte may produce a luminescence reaction of light with a bandwidth that is different from the luminescence produced by the dilution analyte and the volume analyte. Thus, it may be possible to visually differentiate between the image elements produced by the various luminescence reactions.

In some embodiments, processor(s) 1210 may operate to reject a processed image result, for example, if not enough fluid sample was present to perform the test, or if the results are outside of an expected range (for example, the test had been performed outside of a particular temperature range, thus skewing the results).

Example Tests

Example tests that may be conducted using separation device 100 and/or using a method of sedimentation using PVA and/or using a method of separation of blood according to some embodiments will now be described.

Device 100 as described herein is suitable for performing most known blood plasma tests, with particular applicability to test for proteins and antibodies.

As follows is an example of a test for creatinine. All reagents are lyophilized in paper or other hydrophilic porous material that has been treated with hydrophobic patterns to allow fluid to flow through certain circular areas while restricting flow everywhere else. Prior freeze drying of reagents in each layer followed by sandwiching or lamination of multiple layers, lining up the hydrophilic circles, and making a channel, provides the ability to separate reactions once the diluted plasma is presented to the first layer and flows due to hydrophilic forces (or by diffusion) through each layer in its respective channel until the fluid reaches the final readout layer which involves luminescent reagents immobilized on the inner surface of a transparent material such as polyterephthalate. Immobilization techniques can involve lyophilizing the reaction in a 0.1-4% Polyvinyl alcohol mix in suitable buffer such as PBS or TRIS. Gelatin and Pectin in similar dilutions can also be used.

| Channel 1: Patient Creatinine | | |
|---|---|---|
| Layer | Reaction Steps | Conditions |
| 1 | $Creatinine_{patient}$ + H2O → Creatine | Creatininase (amidohyrolase) pH 7.8 |
| 2 | Creatine + ATP → Creatine phosphate +ADP | Creatine Kinase, $Mg^{+2}$ pH 7.8 |
| Readout Layer | Akalumine + O2 + ATP → oxidized Akalumine + CO2 + AMP + diphosphate + hv 677 | Firefly Luciferase, $Mg^{+2}$ pH 7.8 |

In this example, channels two and three (e.g., in a reaction module in a separation device 100) can contain the calibrators. In some embodiments, these calibrators may be contained in a different structure. A small but different amount of creatinine is prior deposited and lyophilized in layer one.

| Layer | Reaction Steps | Conditions |
|---|---|---|
| 1 | Creatinine calibrator + $Creatinine_{patient}$ + H2O → Creatine | Creatininase (amidohyrolase) pH 7.8 |
| 1 | Creatine + ATP → Creatine phosphate + ADP | Creatine Kinase, $Mg^{+2}$, pH 7.8 |
| Readout layer | Akalumine + O2 + ATP → oxidized akalumine + CO2 + AMP + diphosphate + hv 677 | Firefly Luciferase, $Mg^{+2}$, pH 7.8 |

Dilution Factor Test Examples

Examples of dilution factor tests will now be described. These may be conducted using separation device 100 and/or using a method of sedimentation using PVA and/or using a method of separation of blood according to some embodiments.

Phosphoenolpyruvate (PEP) Example

This test can use two calibrators. In this case, a concentration of PEP is added to the diluent and small but different amounts of PEP are lyophilized into the channels of the calibrator. In some embodiments, these channels can be part of a reaction module in a separation device 100 or the PEP is lyophilized into a different structure that can, for example, provide structure for an isolated reaction.

| Layer | Reaction Steps | Conditions |
|---|---|---|
| 1 | 1 PEP + ADP → pyruvic acid + ATP | Pyruvate Kinase pH 7.8 |
| Readout Layer | Akalumine + O2 + ATP → oxidized akalumine + CO2 + AMP + diphosphate + hv 677 | Firefly Luciferase, $Mg^{+2}$ pH 7.8 |

Sarcosine Example:

| Layer | Reaction Steps | Conditions |
|---|---|---|
| 1 | sarcosine + O2 + H2O → glycine + formaldehyde + H2O2 | Sarcosine oxidase pH 7.8 |
| Readout Layer | 2 H2O2 + Luminol → 3APA + light 462 nm | Horseradish Peroxidase pH 7.8 |

Volume Test Example

In enzyme-catalyzed reactions, the reaction rate, within limits, can be directly related to the concentration of the enzyme given that there is an excess of substrate. In CB enzyme catalyzed reactions, the rate of light generated therefore, also can be directly related to the concentration of the enzyme. Therefore, the total intensity of light generated in a certain volume over a time interval can be proportional to the reaction rate, and therefore enzyme concentration, and volume of the fluid. For equal volumes, the total intensity can be used, for example, by a processor, to calculate the concentration of an analyte involved in the reaction, when comparing the intensity generated to that of calibrators. But for differing volumes, the relative difference must be known. In fact, knowing the volume or knowing that the volumes of sample and calibrators are the same can be important in minimizing any error due to volume which can directly impact the accuracy of the analyte test.

In microfluidics, ensuring accurate volumes can be difficult. Air bubbles, small variances in fluidic channels, uneven treatment of any chemical coatings all affect the volume of the fluid in the reaction zones. For clarity, it is not the volume at the reaction zone that can be important, it is the volume of fluid in the zone at the exact time the reaction is measured that can be important.

To compensate for the potential variation in volume of fluid in each zone (more specifically the sample and calibrator zones for each test) at the time the image is captured, for example, by a smartphone camera, in some embodiments, the intensity measurements are normalized with respect to volume. In some embodiments, this is achieved by adding a constant amount of another luminescence species that reacts independently and emits light at a significantly different bandwidth than that of the species used for the sample test. This species can be selected so as to react in the presence of an enzyme (such as alkaline phosphatase) added to the diluent or normally present in plasma.

As noted previously, the total intensity light produced can be directly related to the concentration of the enzyme, within limits, and all other chemical components being equal, the volume. Stated differently, I=k1*E*V where I is intensity, k1 is a constant and E is the concentration of the enzyme and V is the volume of fluid. Where the sample has a concentration of the enzyme, all readout zones can have equal concentrations of the enzyme when fluid eventually gets to that zone. Therefore, any difference in intensity measured is directly proportional to the volume of fluid. And this is the same fluid and volume that is involved in and other independent test being performed in the same zones. Normalization can therefore be provided by dividing the intensity of light generated from the test by the intensity of the volume reaction. So for a test with a sample channel and two calibration channels, embodiments of methods and/or separation devices 100 described herein are configured to adjust the sample intensity to be comparatively the same. Therefore, variances in volumes are minimized as are any error due to volume differences.

In an example, in each zone, a phosphatase substrate, in this example, AquaSpark™ Broad Range Phosphatase, is added to a readout layer as per the Creatinine test example described herein. This substrate reacts in the presence of alk phosphatase (alkaline phosphatase) to produce light centered around 510 nm which, in some embodiments, would be measured in the blue channel of a camera. A specific concentration of alkaline phosphatase enzyme is added to the diluent. This enzyme catalyzes the AquaSpark and causes it to degrade, producing light.

| Layer | Reaction Steps | Conditions |
|---|---|---|
| 1 | $Creatinine_{patient}$ + H2O → Creatine<br>Alkaline Phosphatase in diluent | Creatininase (amidohyrolase) pH 7.8 |
| 2 | Creatine + ATP → Creatine phosphate + ADP<br>Alkaline Phosphatase in diluent | Creatine Kinase, $Mg^{+2}$ pH 7.8 |
| Readout Layer | Akalumine + O2 + ATP → oxidized Akalumine + CO2 + AMP + diphosphate + hv 677<br>AquaSpark decomposition → hv 510 | Firefly Luciferase, $Mg^{+2}$ pH 7.8<br>Alkaline Phosphatase |

This description is made with reference to the separation of plasma from whole blood, however, it is to be understood that the device can be used to separate any suitable filtrate.

In addition to separation of plasma from whole blood, methods of separation using PVA and separation devices according to the present invention can be used in various diagnostic and other medical applications.

It will be apparent to those skilled in the art that various modifications and variations may be made in the materials, devices and methods disclosed herein. It will be understood that elements of embodiments are not necessarily mutually exclusive, and many embodiments can suitably combined with other embodiments.

The examples described above and illustrated are intended to be exemplary only. The description shall be understood to encompass all equivalents.

PARTS LIST

Device 100:
fluid separation component 102
inner container 104
sedimentation compartment 106
fluid sample 107
sample receiving inlet port 108
diluent 109
first aperture (inner container) 110
outer container 112
second aperture (outer container) 114
diluent reservoir 116
outlet 118
reaction module 120
sample obtaining structure 122
cap 124
cap spacer 126
alignment tab 128
mixing ball bearing 130
seal 131
air vent 132
base station 134
reaction module recess 136
Reaction Module 120:
support structure 138
sample receiving structure 140
spreading layer 142
filter layer 144
reagent layer(s) 146
readout layer 148
channel 150a, 150b, 150c
reaction zones 152a, 152b, 152c & 153a, 153b, 153c
adhesive layer 160a, 160b
air vent 162

What is claimed is:

1. A device for separating a fluid into constituent components comprising:
    an inner container forming a sedimentation compartment for receiving a sample of the fluid, the inner container having an inlet port and a first aperture;
    an outer container for receiving the inner container and having a second aperture;
    a breachable diluent reservoir, wherein upon breach an internal volume of the diluent reservoir is in fluid communication with the sedimentation compartment; and
    at least one of the inner container and the outer container being movable between a first configuration where the outer container seals the first aperture and a second configuration wherein the first aperture and the second aperture align to form an outlet for a separated component of the sample fluid;
    wherein the first aperture is sized and shaped such that a volume of sample fluid plus contents of the diluent reservoir will upon settling cover a portion of the first aperture while leaving an air vent at the top.

2. The device of claim 1, wherein the outer container and inner container are cylindrical or cone-shaped.

3. The device of claim 1 comprising indicia for indicating a suitable sample.

4. The device of claim 1 comprising a sample obtaining structure configured to obtain a suitable sample.

5. The device of claim 1, further comprising a cap.

6. The device of claim 5, wherein movement of one or more of the inner container, the outer container or the cap breaches the diluent reservoir.

7. The device of claim 1, wherein the breachable diluent reservoir contains a diluent comprising polyvinyl alcohol (PVA).

8. The device of claim 7, wherein the PVA has a molecular weight between 50,000 and 250,000 Daltons and is 70% to 100% hydrolyzed.

9. A device for separating a fluid into constituent components comprising:
    an inner container forming a sedimentation compartment for receiving a sample of the fluid, the inner container having an inlet port and a first aperture;
    an outer container for receiving the inner container and having a second aperture;
    a breachable diluent reservoir, wherein upon breach an internal volume of the diluent reservoir is in fluid communication with the sedimentation compartment;
    at least one of the inner container and the outer container being movable between a first configuration where the outer container seals the first aperture and a second configuration wherein the first aperture and the second aperture align to form an outlet for a separated component of the sample fluid; and a reaction module in fluid communication with the outlet.

10. The device of claim 9, wherein the reaction module comprises a substrate and at least one reaction zone deposited on the substrate, wherein a reagent system specific for an analyte of interest is deposited in the at least one reaction zone.

11. A method of separating plasma from whole blood using a device for separating a fluid into constituent compartments the device comprising an inner container forming a sedimentation compartment for receiving a sample of the fluid, the inner container having an inlet port and a first aperture; an outer container for receiving the inner container and having a second aperture; a breachable diluent reservoir, wherein upon breach an internal volume of the diluent reservoir is in fluid communication with the sedimentation compartment; and at least one of the inner container and the outer container being movable between a first configuration where the outer container seals the first aperture and a second configuration wherein the first aperture and the second aperture align to form an outlet for a separated component of the sample fluid; and the method comprising:

depositing the whole blood in the sedimentation compartment;

breaching the diluent reservoir; and moving at least one of the inner container and the outer container between the first configuration and the second configuration to form the outlet for the separated plasma.

12. The method of claim 11, wherein breaching the diluent reservoir dilutes the whole blood sample at a ratio of diluent to whole blood of 0.5:1 to 5:1.

* * * * *